US010155311B2

United States Patent
Nakamura et al.

(10) Patent No.: US 10,155,311 B2
(45) Date of Patent: Dec. 18, 2018

(54) METHOD FOR PROCESSING SPECIMEN AND SPECIMEN PROCESSING SYSTEM

(71) Applicant: Kabushiki Kaisha Yaskawa Denki, Kitakyushu-shi (JP)

(72) Inventors: Miki Nakamura, Kitakyushu (JP); Yoshikazu Matsuzaki, Kitakyushu (JP); Makoto Umeno, Kitakyushu (JP)

(73) Assignee: KABUSHIKI KAISHA YASKAWA DENKI, Kitakyushu-shi (JP)

( * ) Notice: Subject to any disclaimer, the term of this patent is extended or adjusted under 35 U.S.C. 154(b) by 99 days.

(21) Appl. No.: 15/221,769

(22) Filed: Jul. 28, 2016

(65) Prior Publication Data
US 2017/0030940 A1 Feb. 2, 2017

(30) Foreign Application Priority Data

Jul. 31, 2015 (JP) .................................. 2015-152866

(51) Int. Cl.
*B25J 9/16* (2006.01)
*B01L 3/00* (2006.01)
(Continued)

(52) U.S. Cl.
CPC ........... *B25J 9/1633* (2013.01); *B01L 3/5021* (2013.01); *G01N 35/0099* (2013.01);
(Continued)

(58) Field of Classification Search
CPC ............ B25J 9/1633; G01N 2035/041; G01N 35/0099; G01N 35/00584;
(Continued)

(56) References Cited

U.S. PATENT DOCUMENTS 7,220,385 B2 * 5/2007 Blecka ............... G01N 35/0099
422/561
9,372,156 B2 * 6/2016 Knight ................. C12Q 1/6851
(Continued)

FOREIGN PATENT DOCUMENTS

| JP | 2005-304303 A | 11/2005 |
| JP | 2010-540927 A | 12/2010 |
| WO | WO 2013/002269 A1 | 1/2013 |

OTHER PUBLICATIONS

Office Action dated Feb. 27, 2018 in Japanese Patent Application No. 2015-152866 with unedited computer generated English translation, 11 pages.
(Continued)

*Primary Examiner* — Jason Holloway
(74) *Attorney, Agent, or Firm* — Oblon, McClelland, Maier & Neustadt, L.L.P.

(57) ABSTRACT

A method for processing a specimen includes controlling a robot to open a lid of a composite container. The composite container includes a first container and a second container. The first container includes a first opening. The second container includes an insertion portion, a protrusion portion, and a second opening. The insertion portion is insertable into the first container through the first opening. The protrusion portion is protrudable through the first opening. The second opening is disposed on the protrusion portion and coverable by the lid. After the lid has been opened, the robot is controlled to take the second container out of the first container. After the second container has been taken out of the first container, the robot is controlled to cover the first opening using the lid.

20 Claims, 18 Drawing Sheets

(51) Int. Cl.
*G01N 35/00* (2006.01)
*G01N 35/04* (2006.01)

(52) U.S. Cl.
CPC ............... *G01N 35/00584* (2013.01); *G01N 2035/00495* (2013.01); *G01N 2035/0405* (2013.01)

(58) Field of Classification Search
CPC .. G01N 2035/00495; G01N 2035/0405; B01L 3/5021
See application file for complete search history.

(56) References Cited

U.S. PATENT DOCUMENTS

| | | | |
|---|---|---|---|
| 2002/0090320 A1* | 7/2002 | Burow | B01L 9/523 422/64 |
| 2005/0123445 A1* | 6/2005 | Blecka | G01N 35/0099 422/64 |
| 2007/0098597 A1* | 5/2007 | Brunner | B01L 9/06 422/400 |
| 2014/0172167 A1* | 6/2014 | Matsukuma | B25J 9/161 700/259 |
| 2014/0241946 A1* | 8/2014 | Self | G01N 35/04 422/65 |

OTHER PUBLICATIONS

"Pole and an extra filtration device", Life Sciences, Japan pole incorporated company, 2011, 16 pages.

\* cited by examiner

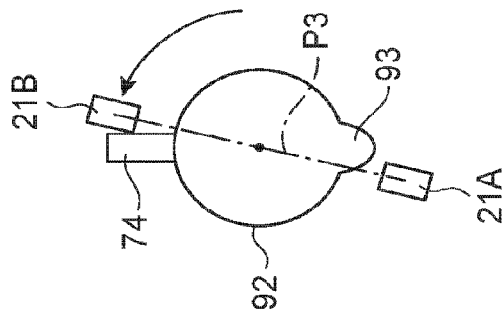
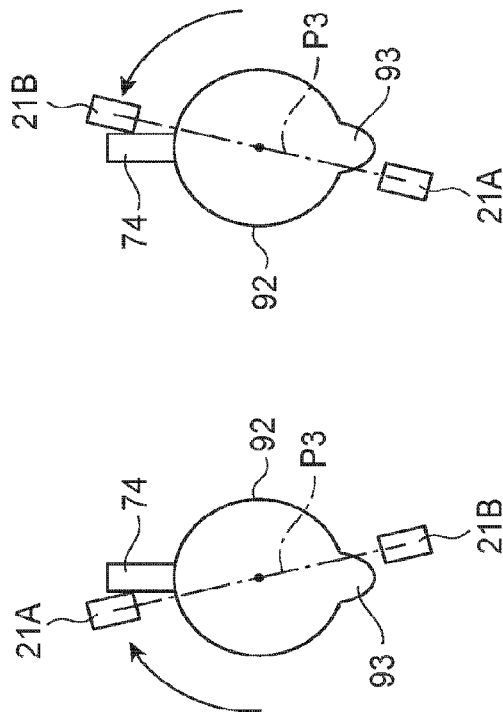
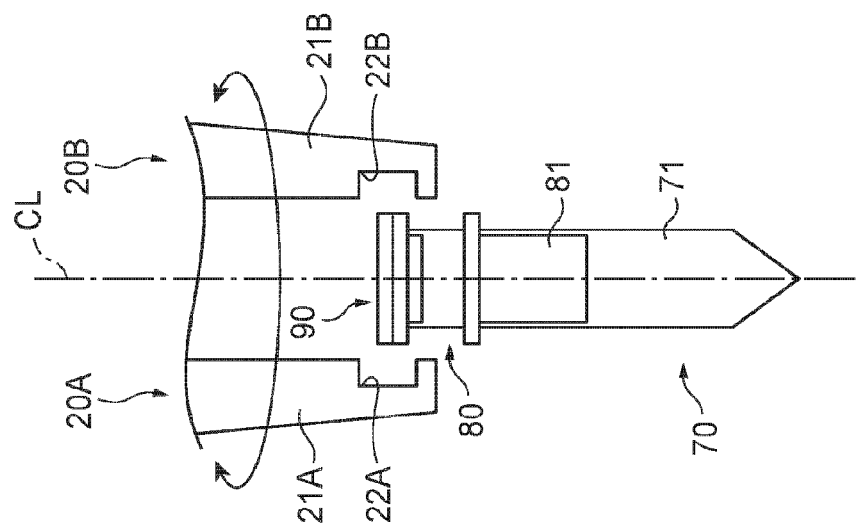

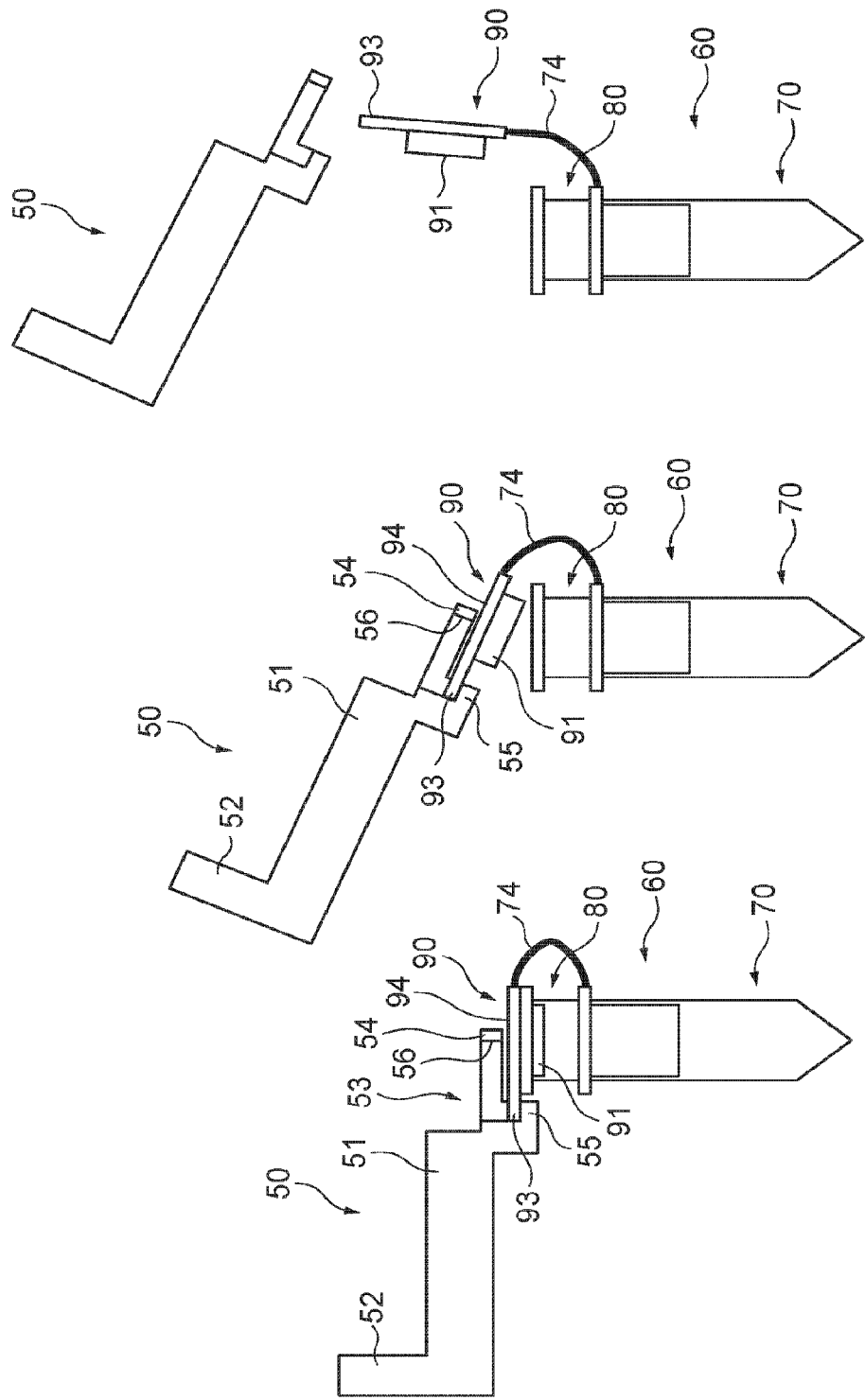

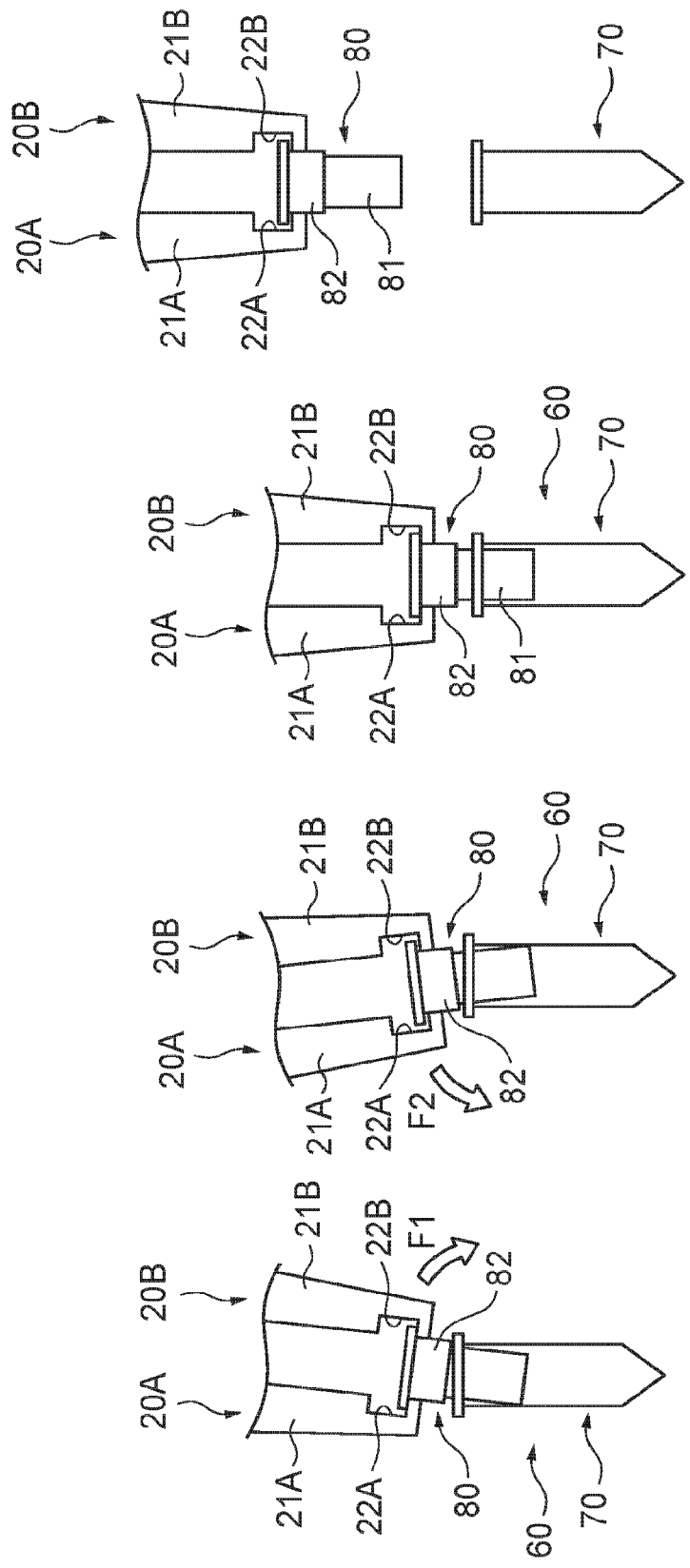

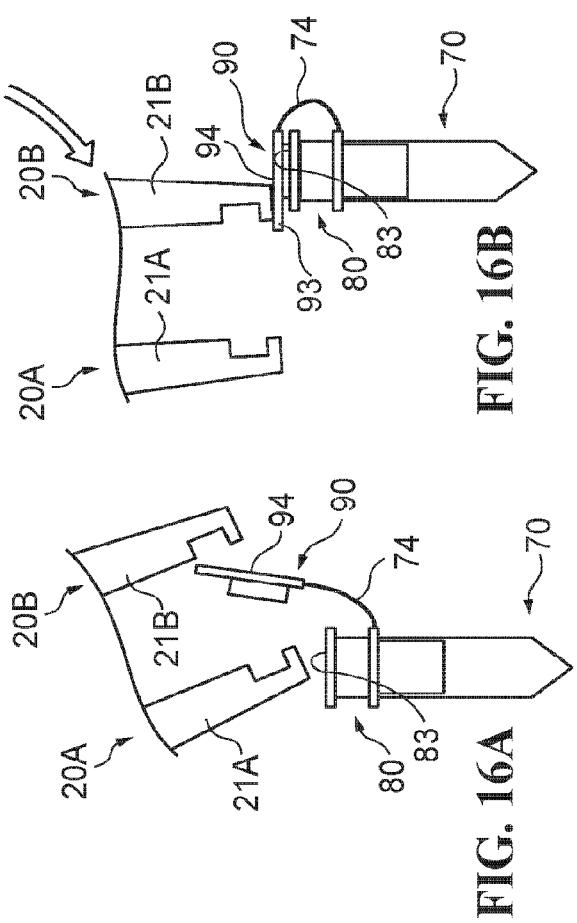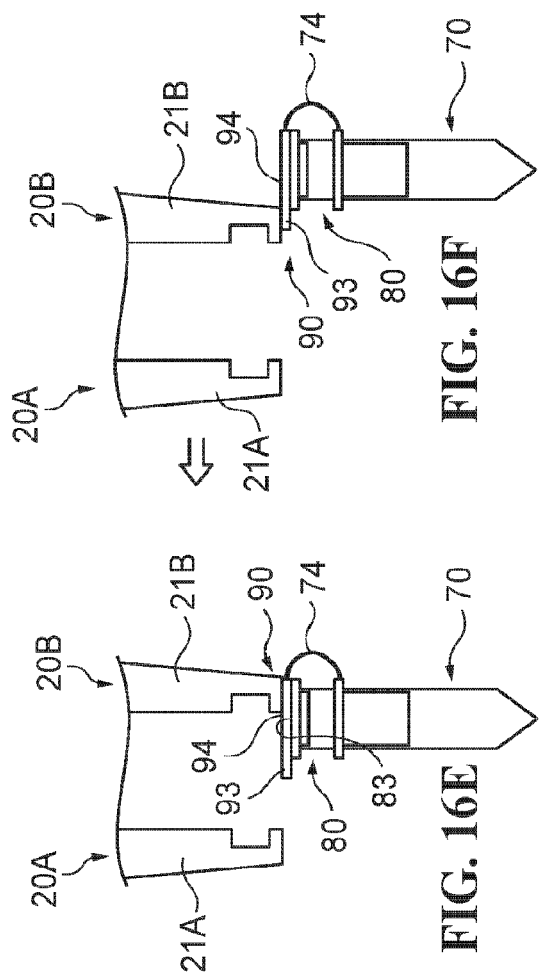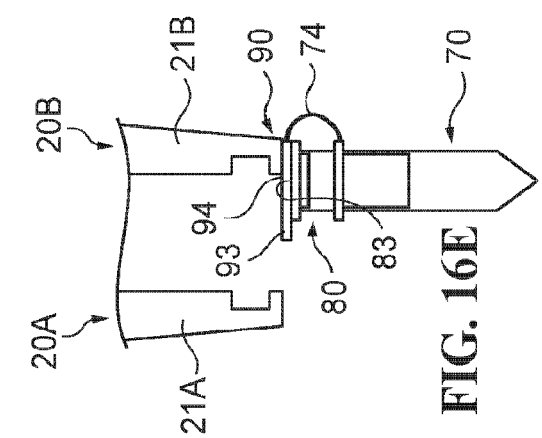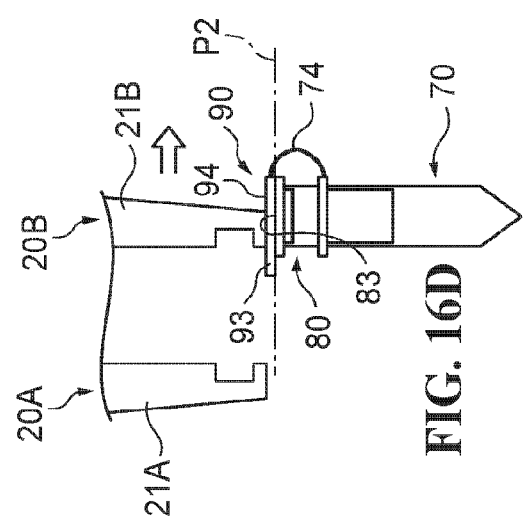

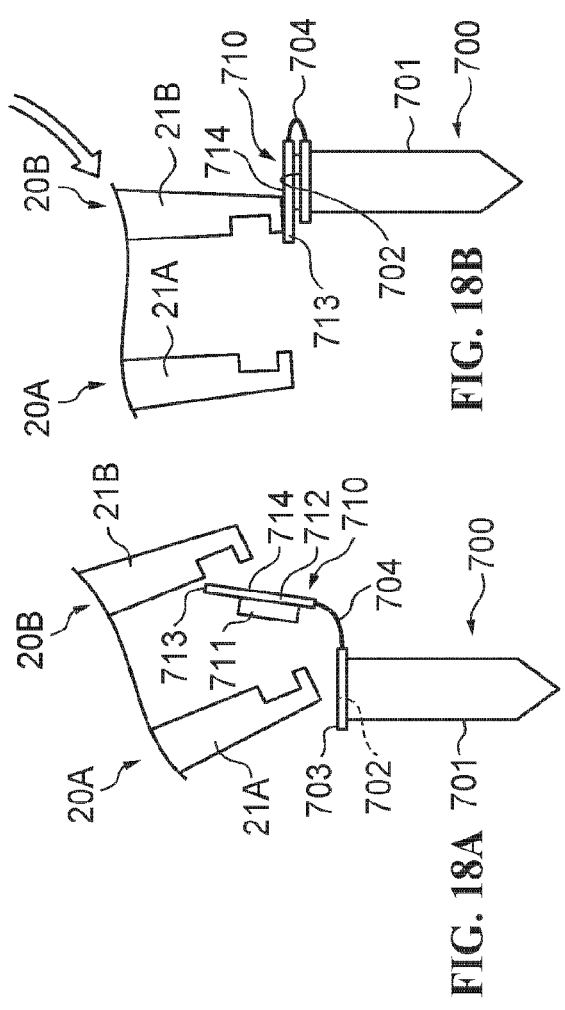
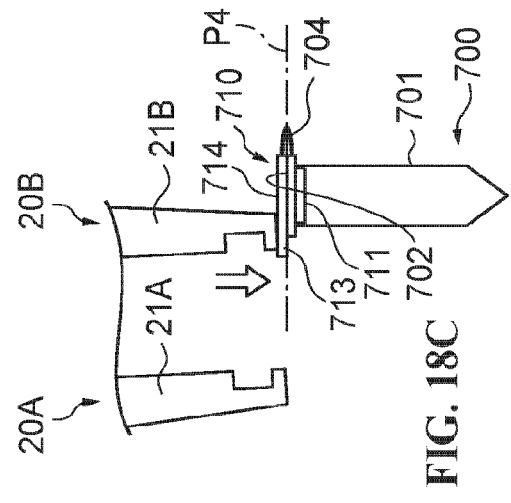
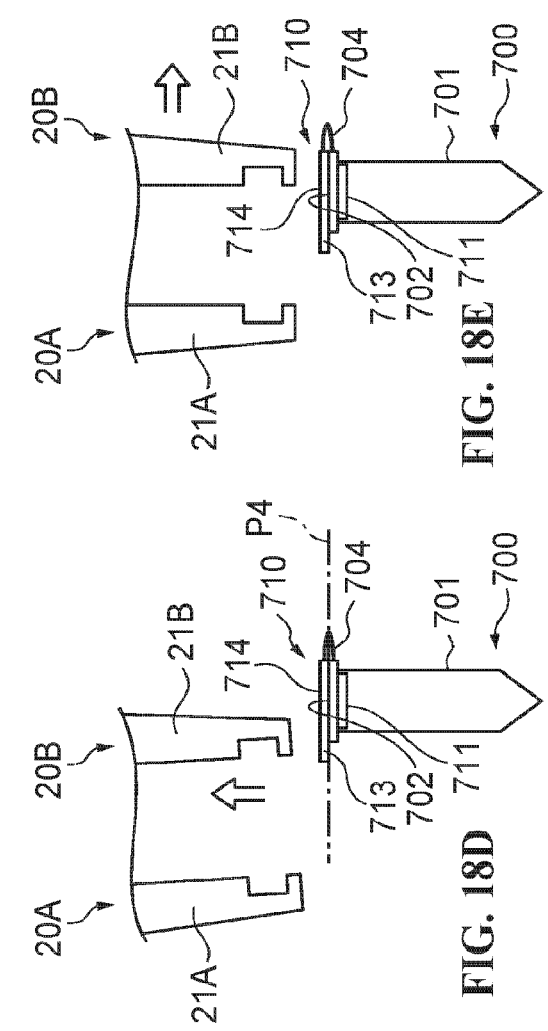
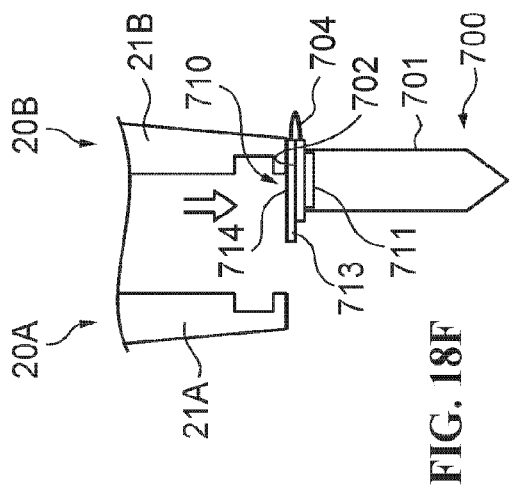
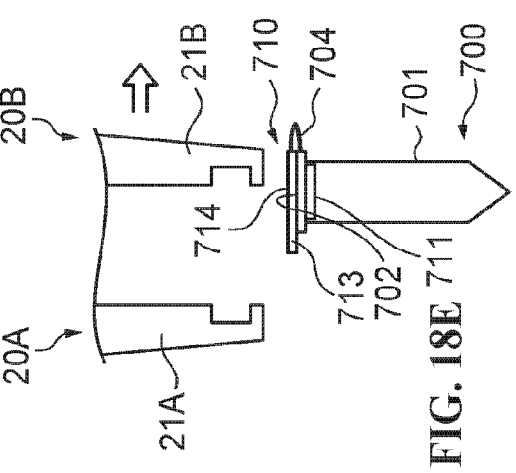
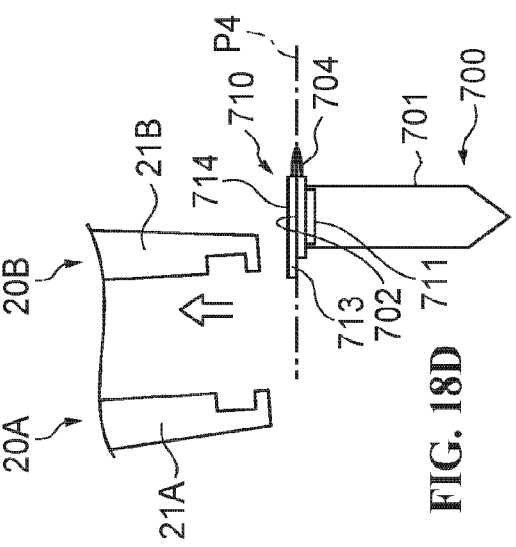

METHOD FOR PROCESSING SPECIMEN AND SPECIMEN PROCESSING SYSTEM

CROSS-REFERENCE TO RELATED APPLICATIONS

The present application claims priority under 35 U.S.C. § 119 to Japanese Patent Application No. 2015-152866, filed Jul. 31, 2015. The contents of this application are incorporated herein by reference in their entirety.

BACKGROUND

Field of the Invention

The embodiments disclosed herein relate to a method for processing a specimen and a specimen processing system.

Discussion of the Background

Japanese Unexamined Patent Application Publication No. 2005-304303 discloses an apparatus that automates specimen processing.

SUMMARY

According to one aspect of the present disclosure, a method for processing a specimen includes controlling a robot to open a lid of a composite container. The composite container includes a first container and a second container. The first container includes a first opening. The second container includes an insertion portion, a protrusion portion, and a second opening. The insertion portion is insertable into the first container through the first opening. The protrusion portion is protrudable through the first opening. The second opening is disposed on the protrusion portion and coverable by the lid. After the lid has been opened, the robot is controlled to take the second container out of the first container. After the second container has been taken out of the first container, the robot is controlled to cover the first opening using the lid.

According to another aspect of the present disclosure, a specimen processing system includes a robot, a lid opening controller, a taking controller, and a lid closing controller. The lid opening controller is configured to control the robot to open a lid of a composite container. The composite container includes a first container and a second container. The first container includes a first opening. The second container includes an insertion portion, a protrusion portion, and a second opening. The insertion portion is insertable into the first container through the first opening. The protrusion portion is protrudable through the first opening. The second opening is disposed on the protrusion portion and coverable by the lid. The taking controller is configured to control the robot to, after the robot has opened the lid, take the second container out of the first container. The lid closing controller is configured to control the robot to, after the robot has taken the second container out of the first container, cover the first opening using the lid.

BRIEF DESCRIPTION OF THE DRAWINGS

A more complete appreciation of the present disclosure and many of the attendant advantages thereof will be readily obtained as the same becomes better understood by reference to the following detailed description when considered in connection with the accompanying drawings, wherein:

FIG. 5 is a perspective view of the rack with the composite container on;

FIGS. 10A, 10B, and 10C are schematics illustrating an operation to align a strap;

FIGS. 13A, 13B and 13C are schematics illustrating an operation to open a lid;

FIGS. 14A, 14B, 14C, and 14D are schematics illustrating an operation to take out a second container;

FIGS. 16A, 16B, 16C, 16D, 16E, and 16F are schematics illustrating an operation to cover a second opening using a lid;

FIGS. 18A, 18B, 18C, 18D, 18E, and 18F are schematics illustrating an operation to cover an opening of a single-body container, without a second container, using a lid.

DESCRIPTION OF THE EMBODIMENTS

Figure 1:
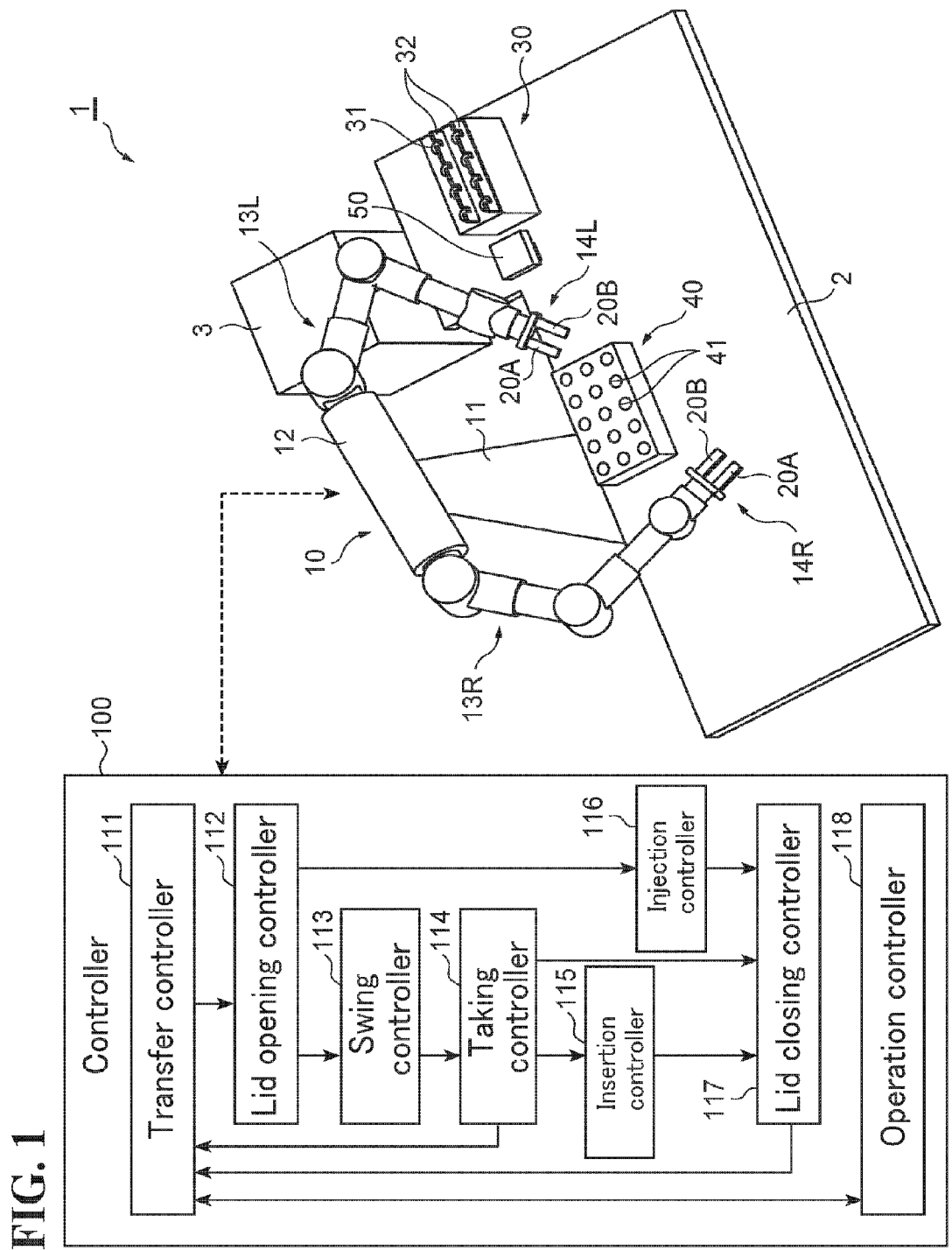
FIG. 1 is a schematic illustrating a configuration of a specimen processing system.

The embodiments will now be described with reference to the accompanying drawings, wherein like reference numerals designate corresponding or identical elements throughout the various drawings.

1. Specimen Processing System

A specimen processing system 1 according to this embodiment performs various kinds of specimen processing including extracting and collecting specimens and is usable in, for example, fields such as biotechnology and medical engineering.

Figure 2:
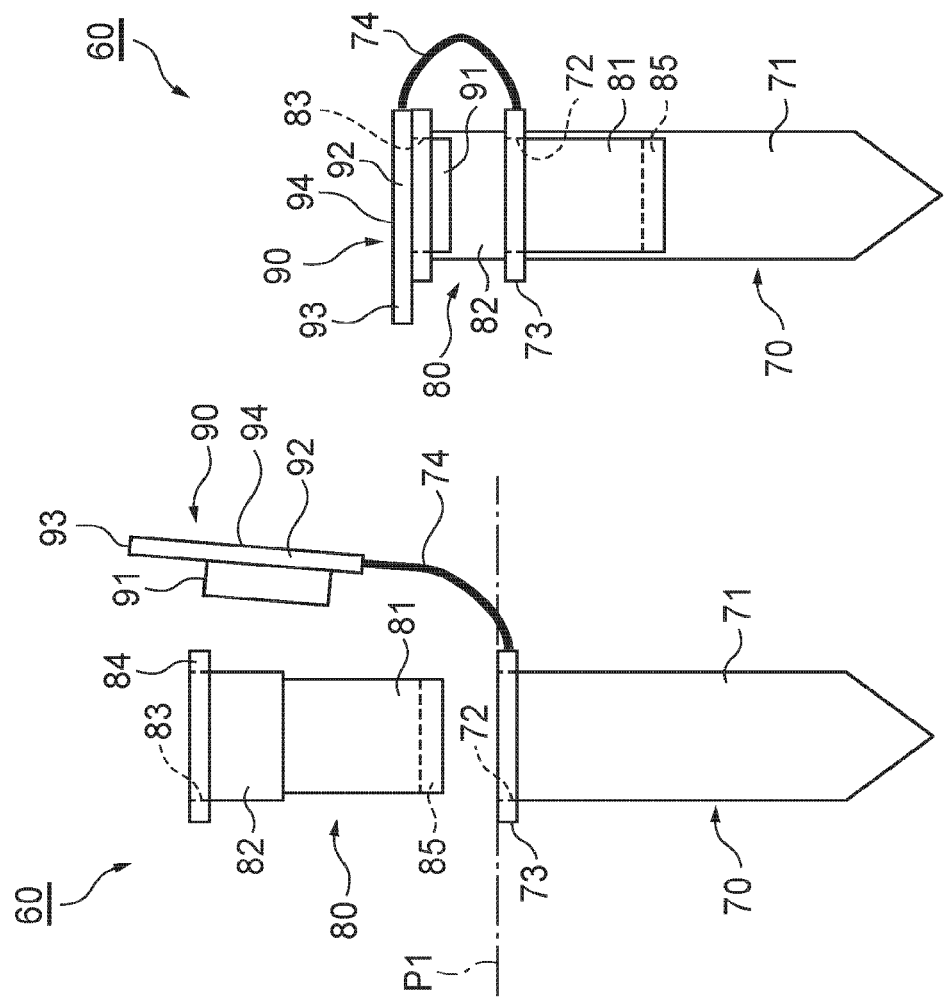
FIGS. 2A, 2B, and 2C are side views of a composite container.

The specimen processing system 1 uses, at least in one or some of the steps of processing, a composite container 60 illustrated in FIGS. 2A, 2B, and 2C. Prior to description of the specimen processing system 1, a configuration of the composite container 60 will be described.

As illustrated in FIGS. 2A, 2B, and 2C, the composite container 60 includes a first container 70, a second container 80, and a lid 90. The first container 70 includes a first opening 72. The first container 70 includes a body 71. In this embodiment, the body 71 has a tubular shape. The body 71 is closed at one end and open at another end to form the first opening 72. In the following description of the composite container 60, the first container 70, and the second container 80, terms such as "downward", "down", "below", and "under" may occasionally be used to refer to the direction toward the closed end of the body 71 and terms such as "upward", "up", and "above" may occasionally be used to refer to the direction toward the open end of the body 71.

The second container 80 includes an insertion portion 81 and a protrusion portion 82. The insertion portion 81 is insertable into the first container 70 through the first opening 72. For example, the insertion portion 81 has a cylindrical structure that has an outer diameter slightly smaller than the inner diameter of the first opening 72. The protrusion portion 82 is connected to an upper portion of the insertion portion 81, and with the insertion portion 81 in place in the first container 70, the protrusion portion 82 is protruding upward from the first container 70 through the first opening 72. In this embodiment, the protrusion portion 82 has a cylindrical structure that has an outer diameter larger than the inner diameter of the first opening 72. The protrusion portion 82 has a second opening 83 on top of the protrusion portion 82. That is, the second container 80 has the second opening 83 on the protrusion portion 82. The inner diameter of the second opening 83 is approximately equivalent to the inner diameter of the first opening 72.

The second container 80 may further include a filter 85. The filter 85 covers the lower end of the insertion portion 81. When a mixture of a plurality of substances is put in the second container 80, the filter 85 adsorbs one or some of the plurality of substances and allows the rest of the plurality of substances to enter the first container 70.

The composite container 60 may further include a first flange 73 and a second flange 84. The first flange 73 surrounds the first opening 72 and extends outward beyond the first container 70. The second flange 84 surrounds the second opening 83 and extends outward beyond the second container 80.

The lid 90 covers the first opening 72 or the second opening 83. In this embodiment, the lid 90 includes a fittable portion 91 and a flange 92. The fittable portion 91 has a cylindrical structure fittable with the inner surface of the first opening 72 or the inner surface of the second opening 83. The flange 92 has a plate structure that is disposed on top of the fittable portion 91 and that extends outward beyond the outer circumference of the fittable portion 91. By contacting the top of the first container 70 or the second container 80, the flange 92 prevents the finable portion 91 from falling deeper into the first container 70 or the second container 80. The lid 90 may include an extending portion 93. The extending portion 93 extends outward from the outer circumference of the flange 92, and thus may be pinched to open and close the lid 90.

The composite container 60 may further include a strap 74. The strap 74 connects the lid 90 to the circumference of the first opening 72 of the first container 70. In this embodiment, the strap 74 is an elastically deformable strip with one end connected to the outer circumference of the first flange 73 and another end connected to the outer circumference of the flange 92. The connection portion at which the strap 74 and the flange 92 are connected to each other is located at a position opposite to the extending portion 93 on the outer circumference of the flange 92.

In this embodiment, the composite container 60 is made of resin material. The composite container 60, which is usable in the specimen processing system 1, will not be limited to the above-described configuration. The composite container 60 may have any other configuration insofar as the composite container 60 includes a first container, a second container, and a lid. The first container includes a first opening. The second container includes an insertion portion, a protrusion portion, and a second opening. The insertion portion is insertable into the first container through the first opening. The protrusion portion is protrudable through the first opening. The second opening is disposed on the protrusion portion and coverable by the lid.

A configuration of the specimen processing system 1 will be described. As illustrated in FIG. 1, the specimen processing system 1 includes a robot 10 and a controller 100. The controller 100 controls the robot 10 to perform at least one or some of the steps of the specimen processing.

(1) Robot

The robot 10 may have any configuration insofar as the robot 10 is capable of pertaining the specimen processing using the composite container 60. For example, the robot 10 may be a single-arm robot or may be a two-arm robot. In the embodiment of FIG. 1, the robot 10 is a two-arm robot. The robot 10 includes a body 11, a shoulder 12, a first arm 13L, and a second arm 13R.

The body 11 stands on the floor surface. The shoulder 12 is mounted top of the body 11 and is turnable about a vertical axis. In this embodiment, the arms 13L and 13R are serial-link type multi-articular arms. The arm 13L is mounted on one end of the shoulder 12, and arm 13R is mounted on another end of the shoulder 12. A hand 14L is mounted on the arm 13L, and a hand 14R is mounted on the arm 13R. The hands 14L and 14R each have two fingers 20A and 20B. Using the two fingers 20A and 20B, the hands 14L and 14R are capable of holding various objects. Examples of the objects that the hands 14L and 14R are capable of holding include, but are not limited to, the first container 70, the second container 80, a lid opening jig 50 (described later), and a dispensing burette.

Figure 3:
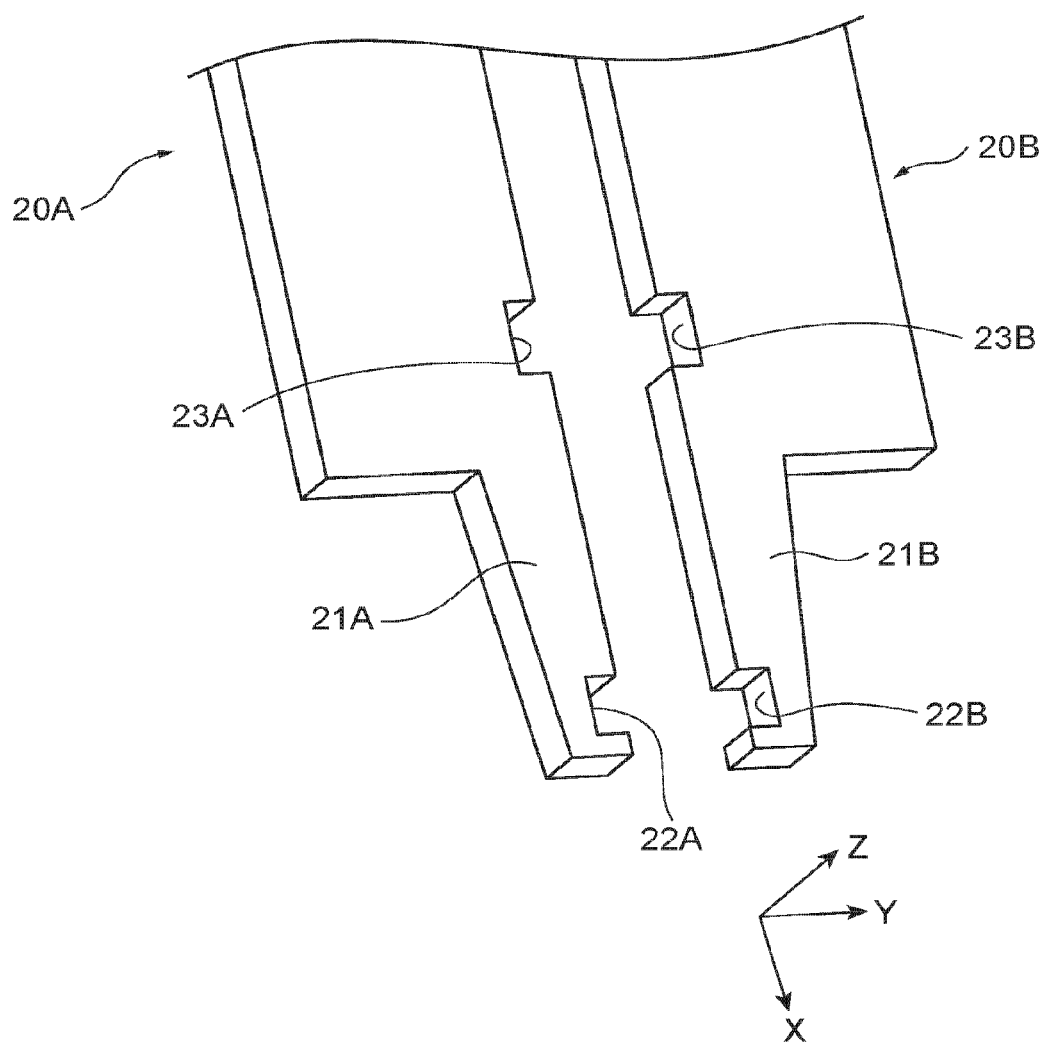
FIG. 3 is a perspective view of fingers.

As illustrated in FIG. 3, the fingers 20A and 20B are opposed to each other and protrude in a direction away from the arms 13L and 13R. The direction in which the fingers 20A and 20B protrude (this direction corresponds to X-axis direction in FIG. 1) will be hereinafter referred to as "longitudinal direction" of the fingers 20A and 20B. The direction in which the fingers 20A and 20B are opposed to each other (this direction corresponds to Y-axis direction in FIG. 1) will be hereinafter referred to as "width direction" of the fingers 20A and 20B. The direction orthogonal to the "longitudinal direction" and the "width direction" (this direction corresponds to Z-axis direction in FIG. 1) will be hereinafter referred to as "thickness direction" of the fingers 20A and 20B. In the following description of the fingers 20A and 20B, the term "distal end" is used to refer to the end opposite to the arms 13L and 13R, and the term "base end" is used to refer to the end by the arms 13L and 13R.

The fingers 20A and 20B respectively include fingertips 21A and 21B. The fingertips 21A and 21B are respectively disposed at the distal ends of the fingers 20A and 20B, and each have a width smaller than the width of the base end.

The finger 20A includes two depressions 22A and 23A. The depressions 22A and 23A are aligned in the longitudinal direction on the edge of the finger 20A on the finger 20B side. The depressions 22A and 23A penetrate through the thickness of the finger 20A, in the thickness direction. The depression 22A is located in the vicinity of the distal end of the fingertip 21A. The depression 23A is located at a position closer to the base end than the fingertip 21A is to the base end.

The finger 20B includes depressions 22B and 23B, which are respectively similar to the depressions 22A and 23A. The depressions 22B and 23B are disposed on the edge of the finger 20B on the finger 20A side. The depression 22B is located in the vicinity of the distal end of the fingertip 21B and is opposed to the depression 22A. The depression 23B is located at a position closer to the base end than the fingertip 21B is to the base end, and is opposed to the depression 23A.

As described later, the depressions 22A and 22B receive the second flange 84 at the time when the fingers 20A and 20B hold the composite container 60. At the time when the fingers 20A and 20B hold the first container 70, the depressions 22A and 22B receive the first flange 73. At the time when the fingers 20A and 20B hold the lid opening jig 50, the depressions 23A and 23B receive a handle 52 of the lid opening jig 50.

(2) Platform and Rack

Referring again to FIG. 1, the specimen processing system 1 may further include a rack 30 and a platform 40. In this embodiment, the rack 30 and the platform 40 are placed on a table 2, which is disposed around the robot 10.

The rack 30 stores at least one container among the composite container 60 and the first container 70. The rack 30 may include a depression to receive the strap 74 of the composite container 60 or the strap 74 of the first container 70.

Figure 4:
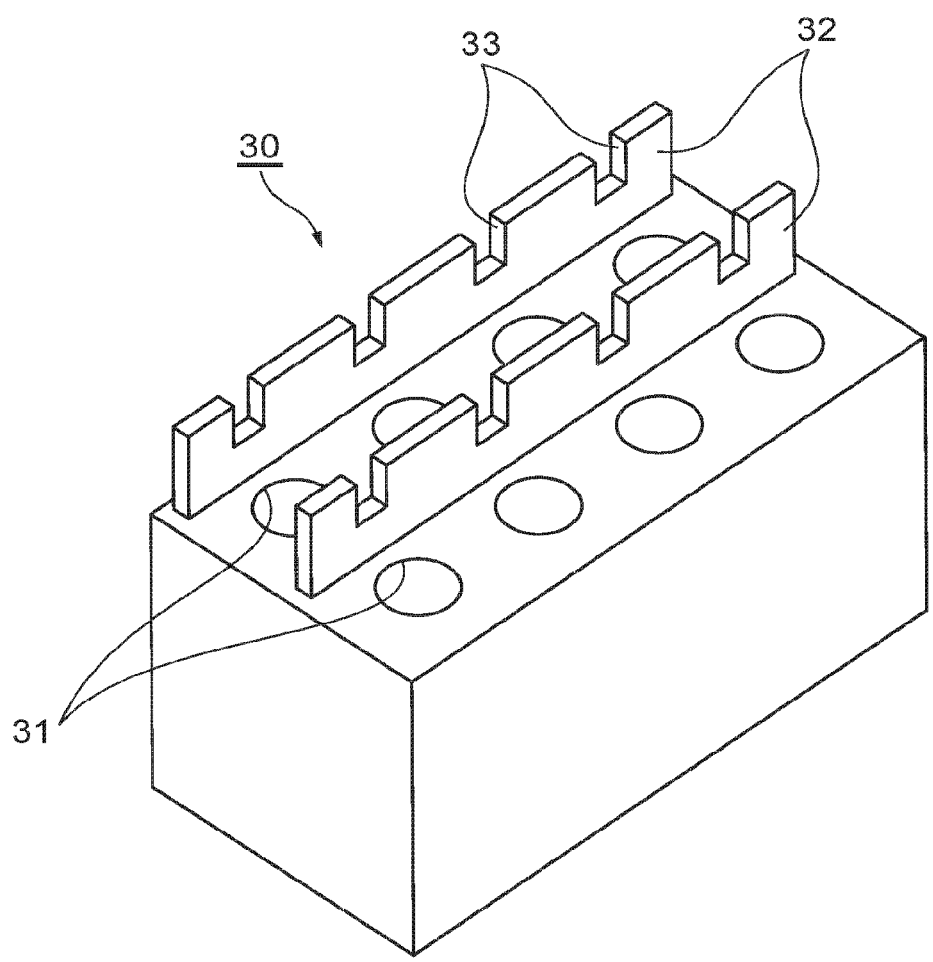
FIG. 4 is a perspective view of a rack.

In the embodiment of FIG. 4, the rack 30 includes a plurality of holes 31 and positioning plates 32. The plurality of holes 31 are open on the upper surface of the rack 30 to receive a lower portion of the composite container 60 or a lower portion of the first container 70. The positioning plates 32 stand at positions adjacent to the plurality of holes 31. Specifically, the positioning plates 32 extend along the rows of the plurality of holes 31 while keeping positions adjacent to the plurality of holes 31. Each positioning plate 32 includes a plurality of depressions 33 on the upper edge of the positioning plate 32. The plurality of depressions 33 respectively correspond to the plurality of holes 31 adjacent to the positioning plate 32. The plurality of holes 31 may form a plurality of rows (two rows in the embodiment of FIG. 4), and each positioning plate 32 may be provided for each row of the plurality of holes 31.

Figure 5:
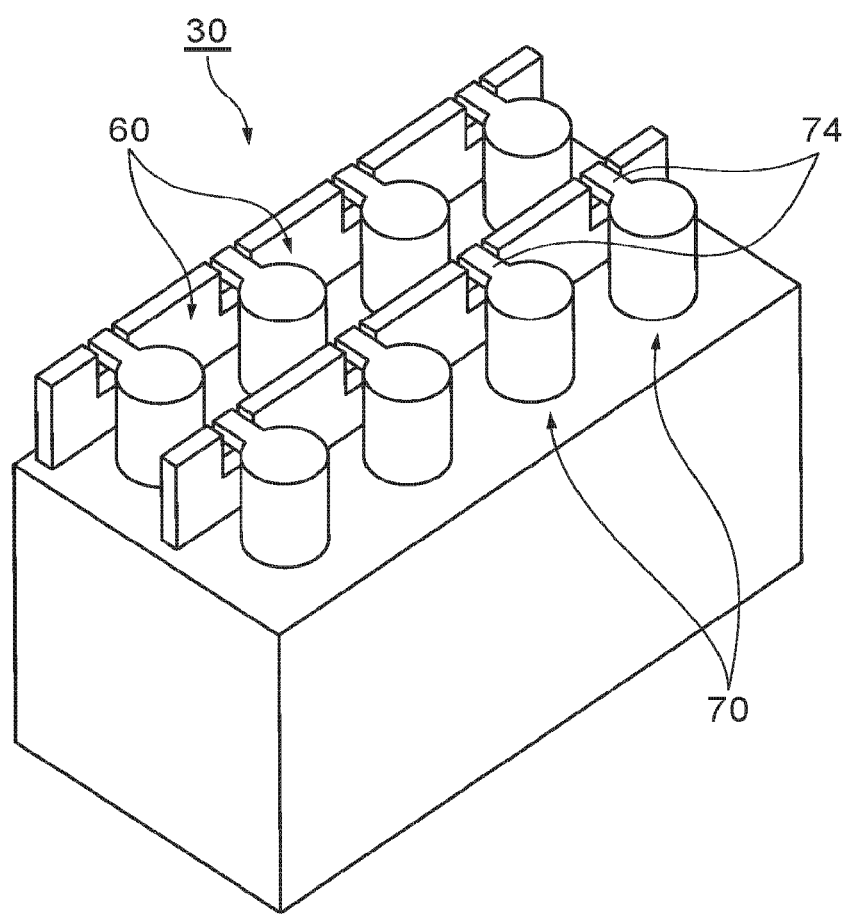

As illustrated in FIG. 5, each depression 33 receives the strap 74 of the composite container 60 or the strap 74 of the first container 70 while the composite container 60 or the first container 70 is stored in the hole 31. This configuration stabilizes the position of the strap 74 while the composite container 60 or the first container 70 is stored in the hole 31.

The platform 40 holds a processing object, namely, at least one container among the composite container 60 and the first container 70 taken out of the rack 30. In the embodiment of FIG. 1, the platform 40 includes a plurality of holes 41. The plurality of holes 41 are open on the upper surface of the platform 40 to receive the lower portion of the composite container 60 or the lower portion of the first container 70. The platform 40 may be equipped with a temperature controller to adjust the internal temperature of the hole(s) 41. For example, the platform 40 may be equipped with a heater to keep the internal temperature of the hole(s) 41 comparatively high, or may be equipped with a cooler to keep the internal temperature of the hole(s) 41 the holes 41 comparatively low.

(3) Lid Opening Jig

Figure 6:
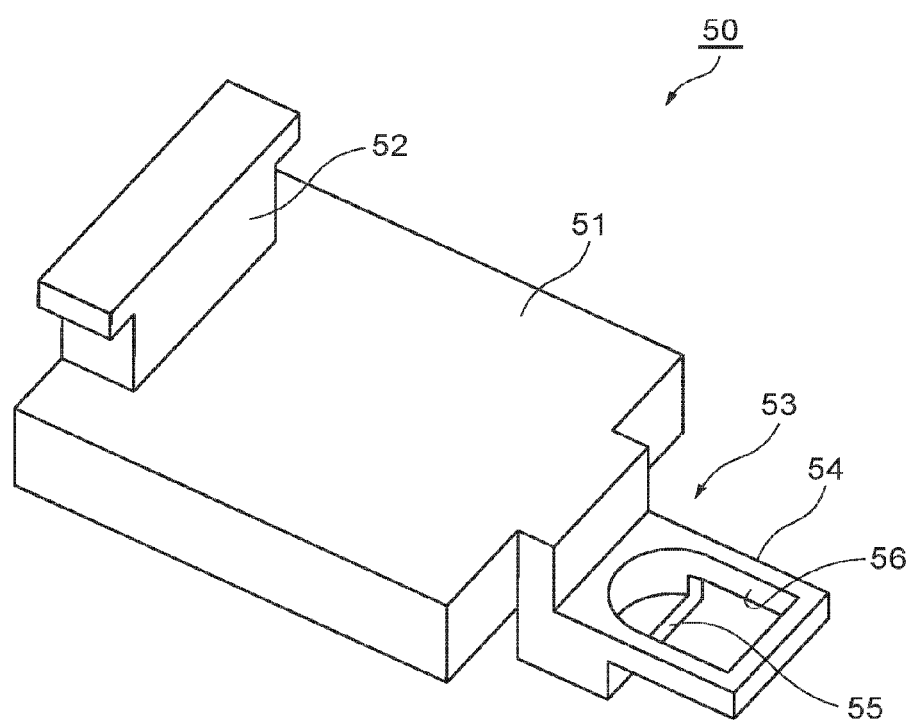
FIG. 6 is a perspective view of a lid opening jig.

The specimen processing system 1 may further include the lid opening jig 50. The lid opening jig 50 is a bottle opener-shaped jig used to open the lid 90 of the composite container 60. In the embodiment of FIG. 6, the lid opening jig 50 includes a base cover 51, the handle 52, and a lip 53.

The handle 52 protrudes from one surface of the base cover 51 and is holdable by the fingers 20A and 20B of the robot 10. The lip 53 protrudes from a surface of the base cover 51 perpendicular to the one surface of the base cover 51 so as to make direct contact with the lid 90. In the following description of the lid opening jig 50, terms such as "upward", "up", and "above" may occasionally be used to refer to the direction in which the handle 52 protrudes from the base cover 51, and terms such as "forward" and "front" may occasionally be used to refer to the direction in which the lip 53 protrudes from the base cover 51.

The lip 53 includes an upper lip 54 and a lower lip 55. The upper lip 54 and the lower lip 55 are apart from each other in the vertical direction and extend in the forward direction. The upper lip 54 extends farther in the forward direction than the lower lip 55. The upper lip 54 includes an opening 56. The opening 56 is open over a range between the area in which the upper lip 54 and the lower lip 55 overlap and the area by which the upper lip 54 extends farther in the forward direction than the lower lip 55.

The lid opening jig 50 is used by the robot 10 to open the lid 90. When the robot 10 opens the lid 90 using the lid opening jig 50, the upper lip 54 is placed over the flange 92, and the lower lip 55 is placed under the extending portion 93. This arrangement enables the lid opening jig 50 to open the lid 90 in a manner similar to the manner in which a bottle opener operates. In this embodiment, while the robot 10 is not operating to open the lid 90, the lid opening jig 50 is placed at a spare space on the table 2 (see FIG. 1).

(4) Centrifugal Separator

Referring again to FIG. 1, the specimen processing system 1 may further include a centrifugal separator. The centrifugal separator 3 is capable of housing the composite container 60 and rotating the composite container 60 to generate centrifugal force so as to force the contents of the composite container 60 into the first container 70 from the second container 80. In this manner, the centrifugal separator 3 promotes the movement of the substance(s) contained in the second container 80 to the first container 70.

(5) Controller

The controller 100 controls the robot 10 to open the lid 90; when the lid 90 is open, controls the robot 10 to take the second container 80 out of the first container 70; and after the second container 80 has been taken out of the first container 70, controls the robot 10 to cover the lid 90 using the first opening 72.

Before the controller 100 controls the robot 10 to take the second container 80 out of the first container 70, the controller 100 may control the robot 10 to alternate effecting a first force to incline the second container 80 in a first direction relative to the first container 70 with effecting a second force to incline the second container 80 in a second direction relative to the first container 70.

The controller 100 may control the robot 10 to insert the second container 80 taken out of the first container 70 into another first container 70, and may control the robot 10 to cover the second opening 83 using the lid 90 of the another first container 70.

In this embodiment, the controller 100 includes such functional modules as a transfer controller 111, a lid opening controller 112, a swing controller 113, a taking controller 114, an insertion controller 115, an injection controller 116, a lid closing controller 117, and an operation controller 118.

The transfer controller 111 controls the robot 10 to transfer the composite container 60, the first container 70, or the second container 80. The lid opening controller 112 controls the robot 10 to open the lid 90 so as to open the first opening 72 or the second opening 83. The swing controller 113 controls the robot 10 to, with the second container 80 resting in the first container 70, alternate effecting the first force to incline the second container 80 in the first direction relative to the first container 70 with effecting the second force to incline the second container 80 in the second direction relative to the first container 70. The taking controller 114 controls the robot 10 to take the second container 80 out of the first container 70. The insertion controller 115 controls the robot 10 to insert the second container 80 taken out of the first container 70 into the another first container 70. The injection controller 116 controls the robot 10 to inject a liquid into the composite container 60. The lid closing controller 117 controls the robot 10 to cover the first opening 72 or the second opening 83 using the lid 90 (that is, close the lid 90). The operation controller 118 controls the robot 10 to operate the centrifugal separator 3.

Figure 7:
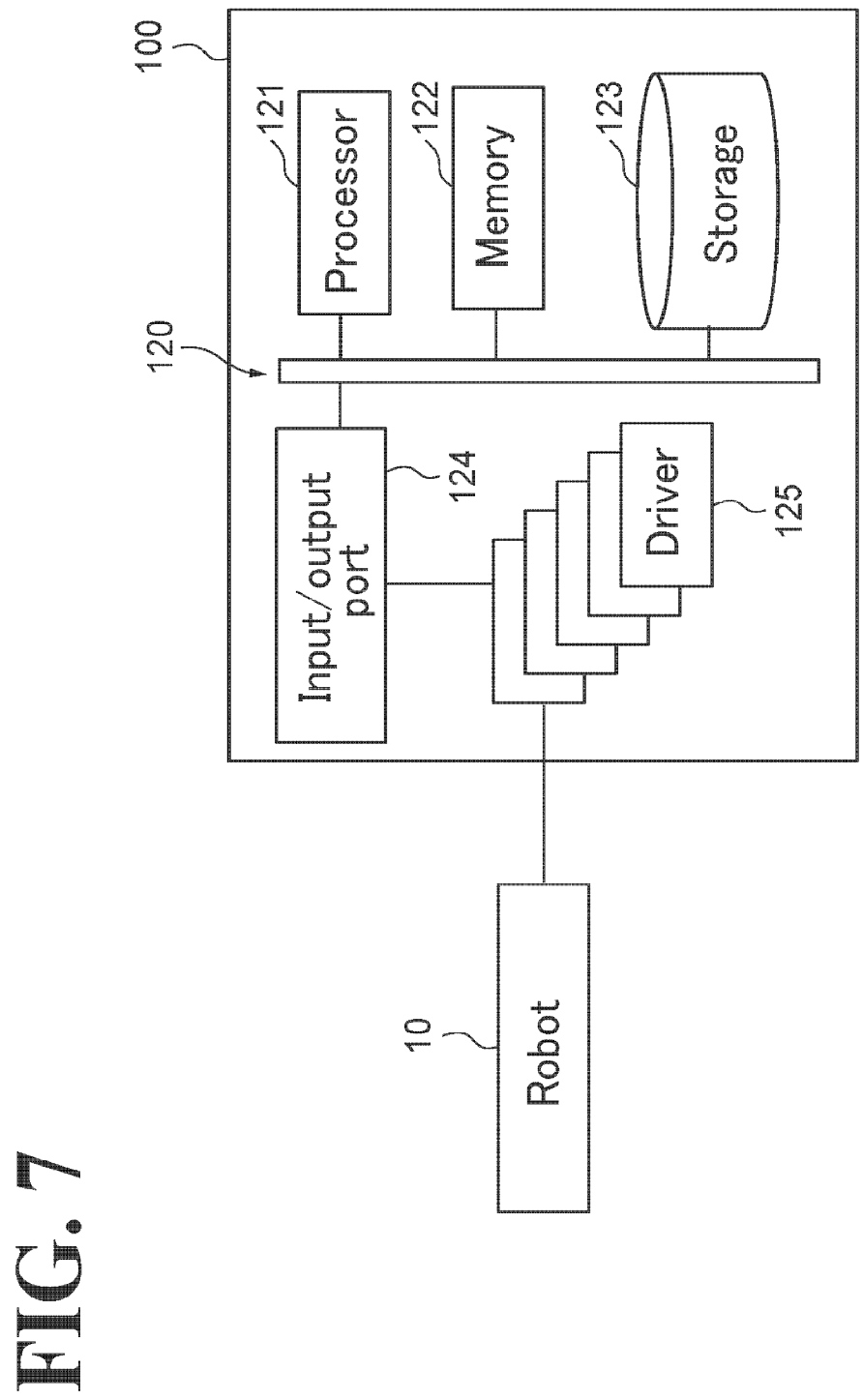
FIG. 7 is a diagram illustrating a hardware configuration of a controller.

In terms of hardware, the controller 100 includes a circuit 120 as illustrated in FIG. 7. The circuit 120 includes a processor 121, a memory 122, a storage 123, an input/output port 124, and a driver 125. The driver 125 is a circuit to drive the actuators of the robot 10. The input/output port 124 inputs and outputs external signals and inputs and outputs signals to and from the driver 125. The processor 121 cooperates with at least one of the memory 122 and the storage 123 to execute a program so as to input and/or output a signal through the input/output port 124. In this manner, the processor 121 implements the above-described functional modules.

It is noted that the hardware configuration of the controller 100 will not be limited to the above-described configuration that executes a program to implement the above-described functional modules. For example, the controller 100 may use a dedicated logic circuit or an ASIC (Application Specific Integrated Circuit) of the dedicated logic circuit to implement the above-described functional modules.

2. Method for Processing Specimen (1) Procedure for Transferring Second Container A procedure for transferring the second container 80 will be described. The procedure for transferring the second container 80 is a non-limiting example of the method for processing a specimen performed by the specimen processing system 1. Assume that the procedure starts under the following conditions. The rack 30 stores a plurality of composite containers 60 each with the second opening 83 covered by the lid 90. The plurality of composite containers 60 have already undergone centrifugal separation in the centrifugal separator 3. That is, a specimen is absorbed on the filter 85 and the rest of the contents are allowed in the first container 70. The rack 30 also stores a plurality of first containers (examples of the another first container 70) that are not combined with second containers 80. Each of these uncombined first containers 70 will be hereinafter referred to as "empty first container 70". The empty first container 70 has its first opening 72 covered by the lid 90.

Figure 8:
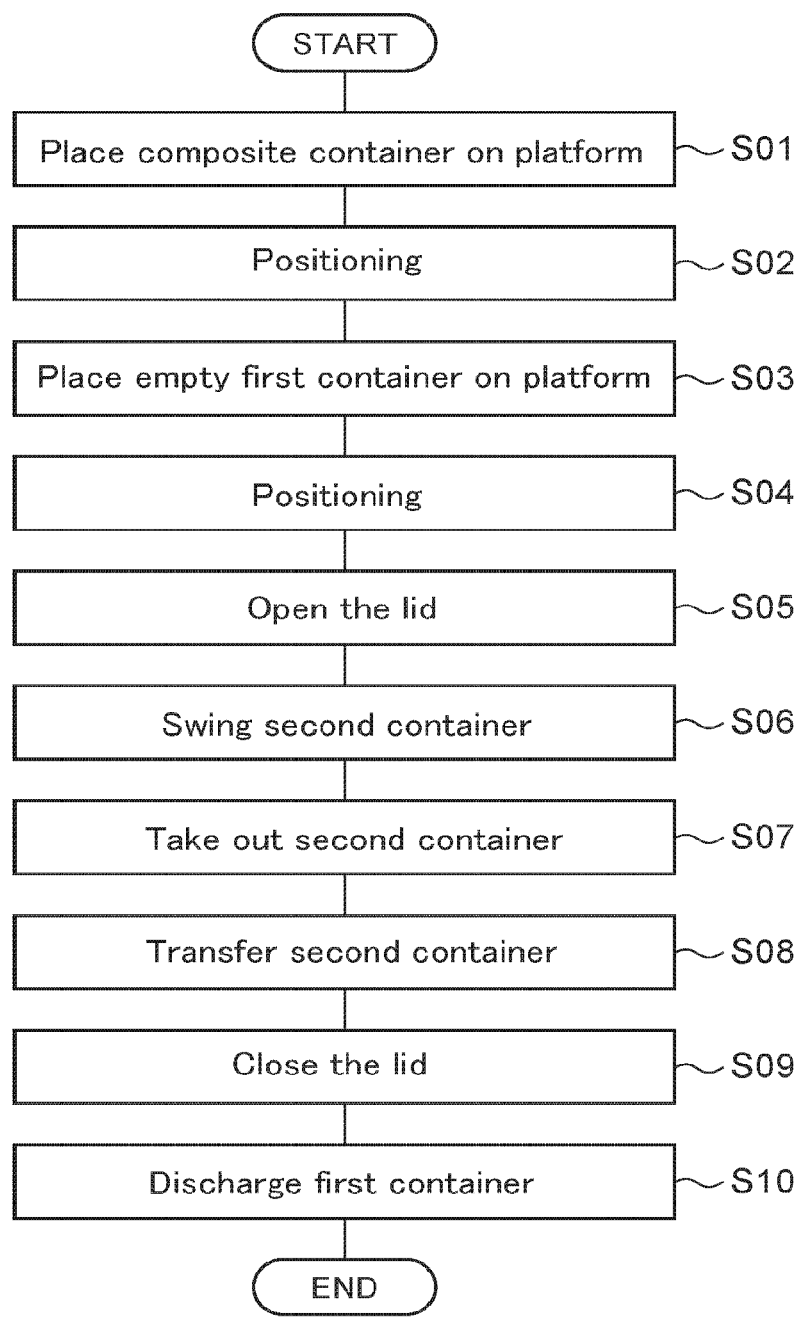
FIG. 8 is a flowchart of a procedure for transferring a second container.

As illustrated in FIG. 8, the controller 100 first performs step S01. At step S01, the transfer controller 111 controls the robot 10 to take one composite container 60 from the rack 30 and transfer the one composite container 60 to the platform 40. For example, the transfer controller 111 controls the robot 10 to pull at least one composite container 60 out of at least one hole 31 of the rack 30, to transfer the at least one composite container 60 to the platform 40, and to insert the at least one composite container 60 into at least one hole 41 of the platform 40.

Figure 9:
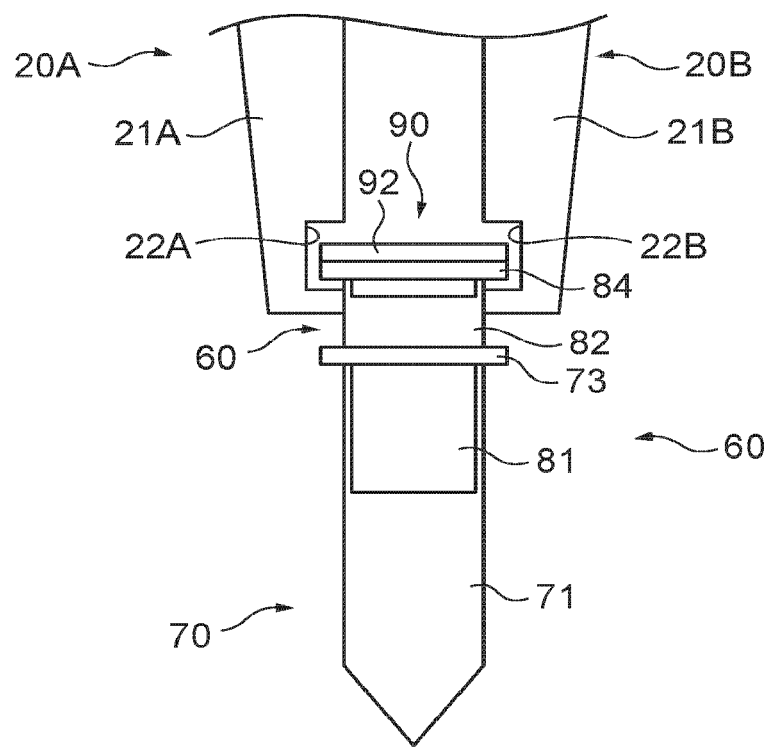
FIG. 9 is a side view of a hand holding the composite container.

The transfer controller 111 may control the robot 10 to hold a portion between the first flange 73 and the second flange 84 so as to transfer the composite container 60. Specifically, as illustrated in FIG. 9, the transfer controller 111 may control the robot 10 to receive the edges of the second flange 84 and the flange 92 at the depressions 22A and 22B and to hold the protrusion portion 82 of the second container 80 at the distal ends of the fingertips 21A and 21B.

Referring again to FIG. 8, the controller 100 then performs step S02. At step S02, the transfer controller 111 controls the robot 10 to perform in positioning of the strap 74 of the composite container 60 transferred to the platform 40.

For example, as illustrated in FIG. 10A, with the composite container 60 transferred to the platform 40, the transfer controller 111 controls the robot 10 to enlarge the gap between the fingers 20A and 20B so as to release the composite container 60.

Then, the transfer controller 111 controls the fingers 20A and 20B to turn in one direction about the center axis, CL, of the composite container 60. For example, as illustrated in FIG. 10B, the transfer controller 111 controls the fingers 20A and 20B to turn in the direction in which the fingertip 21A approaches the strap 74. The angle by which the fingers 20A and 20B turn is set at an angle necessary for making the fingertip 21A contact the strap 74 when the strap 74 is closer to the fingertip 21A than to the fingertip 21B immediately after the composite container 60 is released.

Then, the transfer controller 111 controls the fingers 20A and 20B to turn in the other direction about the center axis CL. For example, as illustrated in FIG. 10C, the transfer controller 111 controls the fingers 20A and 20B to turn in the direction in which the fingertip 21B approaches the strap 74. The angle by which the fingers 20A and 20B turn is set at an angle necessary for making the fingertip 21B contact the strap 74 when the strap 74 is closer to the fingertip 21B than to the fingertip 21A immediately after the composite container 60 is released. This configuration enables the positioning of the strap 74 to be pertained both on the finger 20A side and the finger 20B side.

When the strap 74 can be viewed as being located both on the finger 20A side and the finger 20B side relative to surface P3 (X-Y plane in FIG. 3), which is defined by the fingers 20A and 20B, it is difficult or impossible to perform the positioning of the strap 74 merely by turning the fingers 20A and 20B by some angle. For example, if in FIGS. 10B and 10C the strap 74 were located on the opposite side to the side shown relative to the surface P3 defined by the pre-turned fingers 20A and 20B, the position of the strap 74 after the fingers 20A and 20B have turned would also be located on the opposite side to the side shown (that is, the position of the strap 74 would be on the lower side of FIGS. 10B and 10C). This indicates that, when the strap 74 can be viewed as being located both on the finger 20A side and the finger 20B side relative to the surface P3, the control of the positioning of the strap 74 becomes more complicated. For example, it is necessary to detect the side on which the strap 74 is as viewed relative to the surface P3 and to change the turning angle of the fingers 20A and 20B based on the detection result.

In contrast, in this embodiment, the strap 74 rests in the depression 33 of the rack 30 before step S01, and thus an approximate position of the strap 74 is already determined. Since an approximate position of the strap 74 is already determined before step S01, the side on which the strap 74 is as viewed relative to the surface P3 is known after step S01 as well. This enables the strap 74 to be positioned merely by turning the fingers 20A and 20B by some angle.

Further, the positioning of the strap 74 using the fingers 20A and 20B facilitates the operation to return the composite container 60 to the rack 30, that is, the strap 74 is more readily inserted into the depression 33. This, in turn, facilitates the operation to next time take the composite container 60 to the platform 40, that is, the strap 74 is more readily positioned using the fingers 20A and 20B.

Thus, a combination of the positioning of the strap 74 determined by the depression 33 of the rack 30 with the post-transfer positioning of the strap 74 using the fingers 20A and 20B makes the control to position the strap 74 simpler and more accurate.

The controller 100 may repeat steps S01 and S02 a plurality of times with respect to a plurality of composite containers 60. Specifically, the transfer controller 111 may control the robot 10 to transfer the plurality of composite containers 60 from the rack 30 to the platform 40 and to perform the positioning of the straps 74 of the plurality of composite containers 60.

Referring again to FIG. 8, the controller 100 next performs step S03. At step S03, the transfer controller 111 controls the robot 10 to transfer one empty first container 70 from the rack 30 to the platform 40. For example, the transfer controller 111 controls the robot 10 to pull at least one empty first container 70 out of at least one hole 31 of the rack 30, to transfer the at least one empty first container 70 to the platform 40, and to insert the at least one empty first container 70 into at least one hole 41 of the platform 40.

Figure 11:
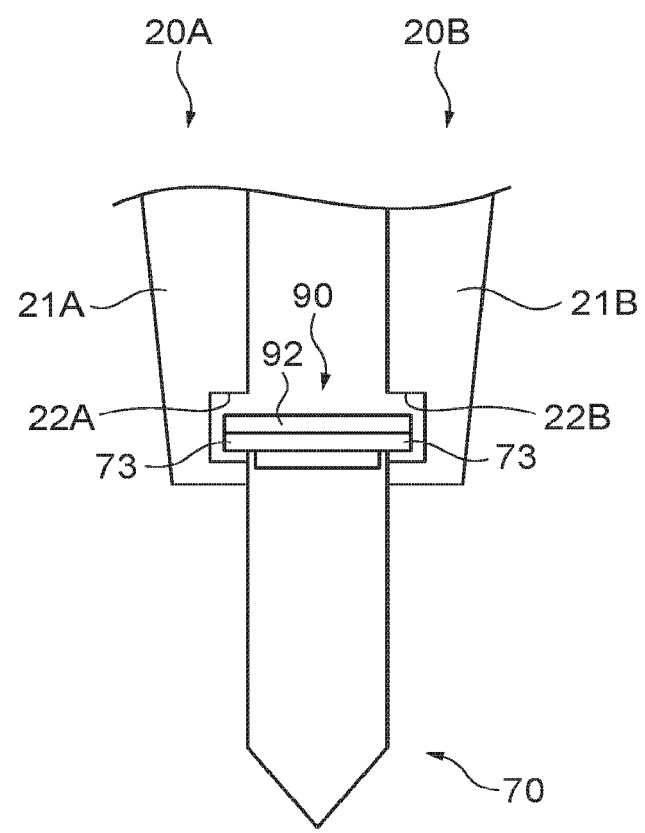
FIG. 11 is a side view of the hand holding a first container.

The transfer controller 111 may control the robot 10 to hold an upper portion of the body 71 so as to transfer the empty first container 70. Specifically, as illustrated in FIG. 11, the transfer controller 111 may control the robot 10 to receive the edges of the first flange 73 and the flange 92 at the depressions 22A and 22B and to hold the upper portion of the body 71 at the distal ends of the fingertips 21A and 21B.

Referring again to FIG. 8, the controller 100 next performs step S04. At step S04, the transfer controller 111 controls the robot 10 to perform positioning of the strap 74 of the empty first container 70 transferred to the platform 40. For example, the transfer controller 111 controls the robot 10 to perform the positioning of the strap 74 by following a procedure similar to the procedure of step S02.

When a plurality of composite containers 60 are placed on the platform 40, the controller 100 may repeat steps S03 and S04 a plurality of times with respect to the same number of empty first containers 70 as the number of the plurality of composite containers 60. Specifically, the transfer controller 111 may control the robot 10 to transfer the same number of empty first containers 70 from the rack 30 to the platform 40 and to perform the positioning of the straps 74 of the same number of empty first containers 70.

Next, the controller 100 performs step S05. At step S05, the lid opening controller 112 controls the robot 10 to open the lid 90 of the composite container 60 and the first container 70 that have been transferred to the platform 40 at steps S01 to S04. For example, the lid opening controller 112 controls the robot 10 to open the lid 90 using the lid opening jig 50.

Figure 12:
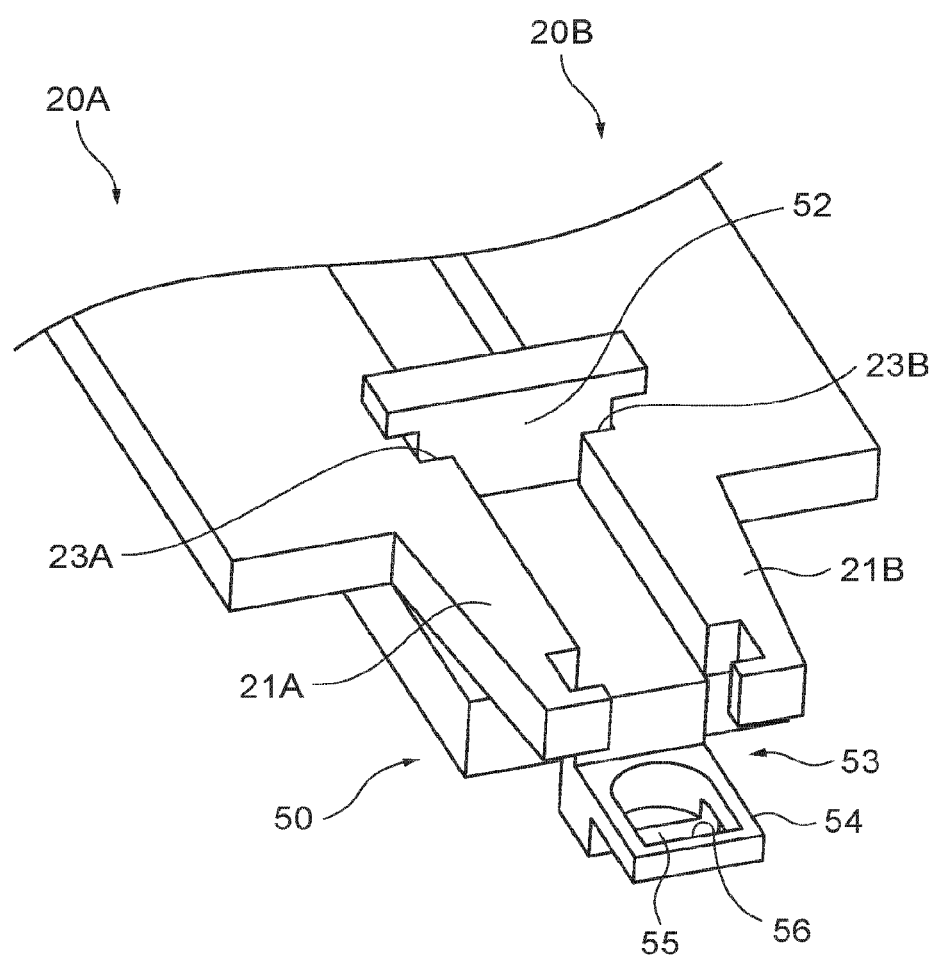
FIG. 12 is a perspective view of the hand holding the lid opening jig.

More specifically, as illustrated in FIG. 12, the lid opening controller 112 controls the robot 10 to hold the lid opening jig 50 using the fingers 20A and 20B. For example, the lid opening controller 112 controls the robot 10 to orient the protruding ends of the fingers 20A and 20B in the forward direction of the lid opening jig 50, to make the depressions 23A and 23B of the fingers 20A and 20B opposed to each other across the handle 52 of the lid opening jig 50, and to hold the handle 52 between the fingers 20A and 20B with the handle 52 fitted in the depressions 23A and 23B.

As illustrated in FIG. 13A, the lid opening controller 112 controls the robot 10 to position the lid opening jig 50 on the opposite side of the strap 74 with the lower lip 55 of the lid opening jig 50 positioned under the extending portion 93 and with the upper lip 54 of the lid opening jig 50 positioned over the lid 90. Then, as illustrated in FIG. 13B, the lid opening controller 112 controls the robot 10 to incline the lid opening jig 50 in the forward direction so as to open the lid 90. Then, as illustrated in FIG. 13C, the lid opening controller 112 controls the robot 10 to move the opening lid 90 over the strap 74 using the lid opening jig 50. While the robot 10 is moving the lid 90 over the strap 74, the opening 56 of the upper lip 54 eliminates or minimizes interference between the extending portion 93 and the upper lip 54.

Referring again to FIG. 8, the controller 100 next performs step S07. At step S07, the taking controller 114 controls the robot 10 to take the second container 80 out of the first container 70 of the composite container 60. After step S01, the controller 100 may perform step S06 before step S01. At step S06, the swing controller 113 controls the robot 10 to alternate effecting the first force to incline the second container 80 in the first direction relative to the first container 70 with effecting the second force to incline the second container 80 in the second direction relative to the first container 70.

By referring to FIGS. 14A, 14B, 14C, and 14D, an exemplary procedure for performing steps S06 and S07 will be described. As illustrated in FIGS. 14A and 14B, the swing controller 113 controls the robot 10 to hold the second container 80 between the fingers 20A and 20B. Specifically, the swing controller 113 controls the robot 10 to receive the second flange 84 at the depressions 22A and 22B and to hold the protrusion portion 82 at the distal ends of the fingertips 21A and 21B. With the protrusion portion 82 held by the distal ends of the fingertips 21A and 21B, the swing controller 113 controls the robot 10 to alternate effecting force F1 to incline the second container 80 toward the finger 20B relative to the first container 70 with effecting force F2 to incline the second container 80 toward the finger 20A relative to the first container 70. The above-described first direction may be a direction toward one finger among the fingers 20A and 20B, and the above-described second direction may be a direction toward the other finger.

By alternating effecting force F1 with effecting force F2, the engagement between the first container 70 and the second container 80 is released or loosened, improving reliability in taking the second container 80 out of the first container 70. It is noted that to alternate effecting force F1 with effecting force F2 encompasses to effect force F1 once and effect force F2 once. There is no limitation to the number of times to effect forces F1 and F2.

As illustrated in FIGS. 14A, 14B, and 14C, controlling the robot 10 to alternate effecting force F1 with effecting force F2 may include controlling the robot 10 to move the protrusion portion 82 away from the first container 70 while alternating effecting force F1 with effecting force F2.

Upon completion of the operation to alternate effecting force F1 to the second container 80 with effecting force F2 to the second container 80, the taking controller 114 controls the robot 10 to take the second container 80 held by the fingers 20A and 20B out of the first container 70.

Referring again to FIG. 8, the controller 100 next performs step S08. At step S08, the insertion controller 115 controls the robot 10 to transfer the second container 80 that has been taken out at step S07 and to insert the second container 80 into the empty first container 70. In the case where a plurality of composite containers 60 and a plurality of other first containers 70 are placed on the platform 40, the controller 100 may repeat steps S06 to S08 a plurality of times with respect to the plurality of composite containers 60 and the plurality of other first containers 70. Specifically, the swing controller 113, the taking controller 114, and the insertion controller 115 may control the robot 10 to perform the operation to transfer the second container 80 with respect to the plurality of composite containers 60 and the plurality of other first containers 70.

In the following description, the first container 70 from which the second container 80 has been removed will be referred to as "empty first container 70", and the first container 70 with the second container 80 on will be referred to as composite container 60".

Next, the controller 100 performs step S09. At step S09, the lid closing controller 117 controls the robot 10 to cover the first opening 72 of the empty first container 70 using the lid 90, which is connected to the first container 70.

As illustrated in FIGS. 15A, 15B, 15C, 15D, 15E, and 15F, controlling the robot 10 to cover the first opening 72 using the lid 90 may include controlling the robot 10 to move the lid 90 to a position corresponding to the first opening 72; controlling the robot 10 to cause a portion of the robot 10 contacting the outer surface of 94 of the lid 90 to move toward the first opening 72; and after the portion of the robot 10 contacting the outer surface of 94 of the lid 90 has moved to the first opening 72, controlling the robot 10 to cause the portion of the robot 10 contacting the outer surface of 94 of the lid 90 to move along plane P1 of the first opening 72.

The outer surface of 94 of the lid 90 refers to the outer surface of the lid 90 that is opposite to the first opening 72 or the second flange 84 covered by the lid 90. In this embodiment, the outer surface 94 corresponds to the surface of the flange 92 opposite to the fittable portion 91 (see FIGS. 2A, 2B, and 2C). The plane P1 of the first opening 72 refers to the open surface of the first opening 72 (for example, the top surface of the body 71).

Figures 15A, 15B, 15C, 15D, 15E, 15F:
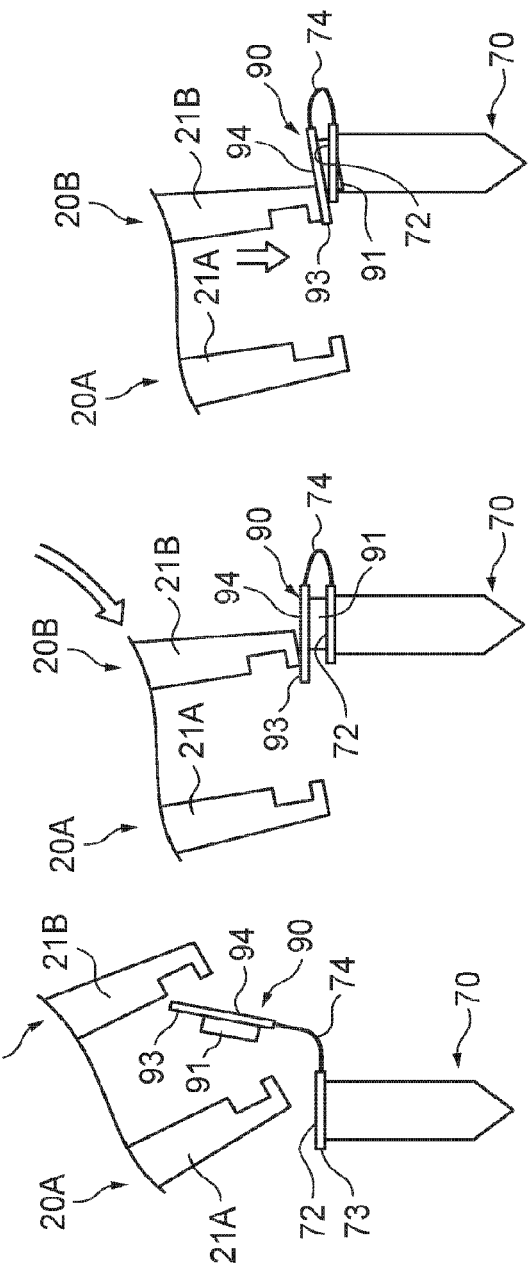
FIGS. 15A, 15B, 15C, 15D, 15E, and 15F are schematics illustrating an operation to cover a first opening using the lid.

In this embodiment, as illustrated in FIG. 15A, the lid closing controller 117 controls the robot 10 to position the fingers 20A and 20B on both sides of the standing lid 90. Then, as illustrated in FIG. 15B, the lid closing controller 117 controls the robot 10 to contact the lid 90 using the distal end of the finger 20B, which is on the side of the outer surface of 94 of the lid 90, and to move the lid 90 to a position at which to cover the first opening 72.

Then, as illustrated in FIG. 15C, the lid closing controller 117 controls the robot 10 to make the distal end of the finger 20B contact the extending portion 93 of the outer surface 94 and to move the distal end of the finger 20B toward the first opening 72. The lid closing controller 117 controls the robot 10 to cause the distal end of the finger 20B to move toward the first opening 72 so as to press at least one portion of the fittable portion 91 to a deepest possible position in the first opening 72. For example, the lid closing controller 117 controls the robot 10 to cause the distal end of the finger 20B to move toward the first opening 72 to a distance at which a portion of the lid 90 unfitted in the first opening 72 is interfered and another portion of the lid 90 completely fitted in the first opening 72 is not interfered. More specifically, the lid closing controller 117 controls the robot 10 to make the distal end of the finger 20B move to a distance equivalent to the thickness of the flange 92 so as to approach the top surface of the body 71. By moving the finger 20B toward the first opening 72, the extending portion 93 side of the lid 90 is pressed toward the first opening 72 and the extending portion 93 side of the fittable portion 91 is pressed into the first opening 72.

Then, as illustrated in FIGS. 15D and 15E, the lid closing controller 117 controls the robot 10 to cause the distal end of the finger 20B to move toward the strap 74 along the plane P1 while keeping the distal end of the finger 20B by the first opening 72. While the distal end of the finger 20B is moving toward the strap 74, a portion of the lid 90 off the first opening 72 is pressed into the first opening 72 by the distal end of the finger 20B. Once the portion of the lid 90 is pressed into the first opening 72, the portion of the lid 90 is prevented from rising off the first opening 72 by the distal end of the finger 20B. This configuration reliably presses the fittable portion 91 into the first opening 72, making the lid 90 tightly secured in the first opening 72 and ensuring reliability in covering the first opening 72.

Then, as illustrated in FIG. 15F, the lid closing controller 117 controls the robot 10 to cause the distal end of the finger 20B to move along the plane P1 in a direction away from the strap 74. This ensures that even if some portion of the lid 90 rises after the finger 20B has passed by, the portion is again pressed into the first opening 72, making the lid 90 more tightly secured in the first opening 72 and thus improving reliability in covering the first opening 72.

As illustrated in FIGS. 15A, 15B, 15C, 15D, 15E, and 15F, controlling the robot 10 to cause a portion of the robot 10 to move along the plane P1 of the first opening 72 may include controlling the robot 10 to cause the portion of the robot 10 to reciprocate between the side of the strap 74 (which is a non-limiting example of the first side of the plane by the strap recited in the appended claims) and the side opposite to the strap 74 (which is a non-limiting example of the second side of the plane opposite to the first side recited in the appended claims).

At step S09, the lid closing controller 117 may control the robot 10 to cover the second opening 83 of the composite container 60 using the lid 90 of the composite container 60. Specifically, the lid closing controller 117 may control the robot 10 to cover the second opening 83 using the lid 90 connected to the another first container 70.

As illustrated in FIGS. 16A, 16B, 16C, 16D, 16E, and 16F, controlling the robot 10 to cover the second opening 83 using the lid 90 may include controlling the robot 10 to, similarly to covering the first opening 72 using the lid 90, move the lid 90 to a position corresponding to the second opening 83; controlling the robot 10 to cause a portion of the robot 10 contacting the outer surface of 94 of the lid 90 to move toward the second opening 83; and after the portion of the robot 10 contacting the outer surface of 94 of the lid 90 has moved to the second opening 83, controlling the robot 10 to cause the portion of the robot 10 contacting the outer surface of 94 of the lid 90 to move along plane P2 of the second opening 83. The plane P2 of the second opening 83 refers to the open surface of the second opening 83 (for example, the top surface of the protrusion portion 82).

In this embodiment, as illustrated in FIG. 16A, the lid closing controller 117 controls the robot 10 to position the fingers 20A and 20B on both sides of the standing lid 90. Then, as illustrated in FIG. 16B, the lid closing controller 117 controls the robot 10 to contact the lid 90 using the distal end of the finger 20B, which is on the side of the outer surface of 94 of the lid 90, and to move the lid 90 to a position at which to cover the second opening 83.

Then, as illustrated in FIG. 16C, the lid closing controller 117 controls the robot 10 to make the distal end of the finger 20B contact the extending portion 93 of the outer surface 94 and to move the distal end of the finger 20B toward the second opening 83. The lid closing controller 117 controls the robot 10 to cause the distal end of the finger 20B to move toward the second opening 83 so as to press at least one portion of the fittable portion 91 to a deepest possible position in the second opening 83. For example, the lid closing controller 117 controls the robot 10 to cause the distal end of the finger 20B to move toward the second opening 83 to a distance at which a portion of the lid 90 unfitted in the second opening 83 is interfered and another portion of the lid 90 completely fitted in the second opening 83 is not interfered. More specifically, the lid closing controller 117 controls the robot 10 to make the distal end of the finger 20B move to a distance equivalent to the thickness of the flange 92 so as to approach the top surface of the protrusion portion 82. By moving the finger 20B toward the second opening 83, the extending portion 93 side of the lid 90 is pressed toward the second opening 83 and the extending portion 93 side of the fittable portion 91 is pressed into the second opening 83.

Then, as illustrated in FIGS. 16D and 16E, the lid closing controller 117 controls the robot 10 to cause the distal end of the finger 20B to move toward the strap 74 along the plane P2 while keeping the distal end of the finger 20B by the second opening 83. Then, as illustrated in FIG. 16F, the lid closing controller 117 controls the robot 10 to cause the distal end of the finger 20B to move along the plane P2 in a direction away from the strap 74. Following this procedure improves reliability in covering the second opening 83, similarly to the improved reliability in covering the first opening 72 using the lid 90.

Next, the controller 100 performs step S10. At step S10, the transfer controller 111 controls the robot 10 to hold and transfer the empty first container 70, similarly to step S03, and to discharge the empty first container 70. Thus, following the procedure for transferring the second container 80 ends.

(2) Procedure for Collecting Specimen

A procedure for collecting a specimen will be described. The procedure for collecting a specimen is a non-limiting example of the method for processing a specimen pertained by the specimen processing system 1. Assume that the procedure starts under the following conditions. Specifically, a plurality of composite containers 60 that have undergone steps S01 to S10 remain on the platform 40. As described above, specimens are absorbed on the filters 85 of the plurality of composite containers 60.

Figure 17:
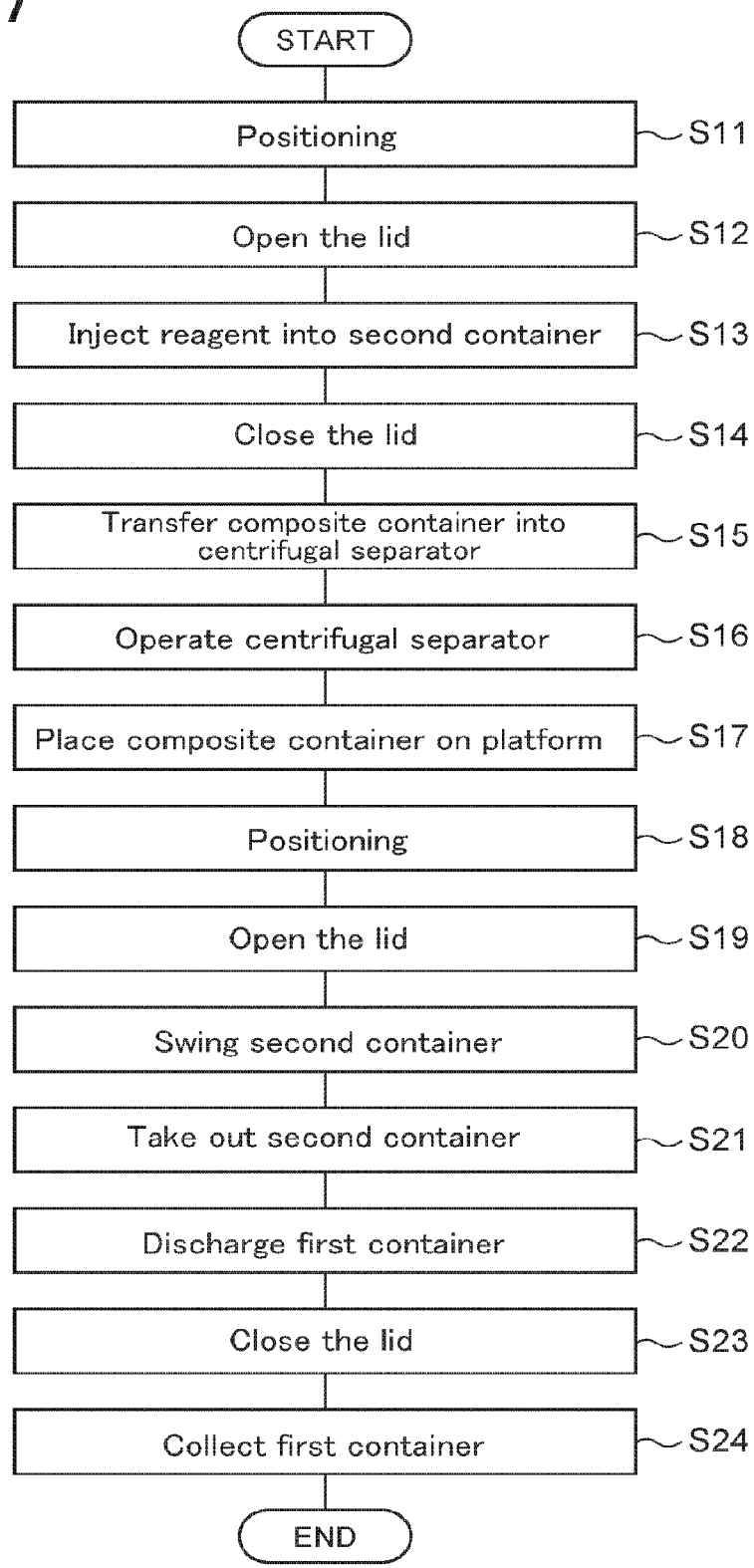
FIG. 17 is a flowchart of a procedure for collecting a specimen.

As illustrated in FIG. 17, the controller 100 first performs step S11. At step S11, the transfer controller 111 controls the robot 10 to perform positioning of the strap 74 of a composite container 60 held in the platform 40. For example, the transfer controller 111 controls the robot 10 to perform the positioning of the strap 74 by following a procedure similar to the procedure of step S02.

Next, the controller 100 performs step S12. At step S12, the lid opening controller 112 controls the robot 10 to open the lid 90 of the composite container 60. For example, the lid opening controller 112 controls the robot 10 to open the lid 90 by following a procedure similar to the procedure of step S05.

Next, the controller 100 performs step S13. At step S13, the injection controller 116 controls the robot 10 to inject a reagent into the second container 80 through the second opening 83 using, for example, a dispensing burette (not illustrated) such as a pipette and a syringe. A non-limiting example of the reagent is a liquid to dissolve the specimen absorbed on the filter 85.

Next, the controller 100 performs step S14. At step S14, the lid closing controller 117 controls the robot 10 to cover the second opening 83 of the composite container 60 using the lid 90 of the composite container 60. For example, the lid closing controller 117 controls the robot 10 to cover the second opening 83 using the lid 90 by following a procedure similar to the procedure of step S09.

Next, the controller 100 performs step S15. At step S15, the transfer controller 111 controls the robot 10 to hold the composite container 60 on the platform 40, similarly to step S01, and to transfer the composite container 60 into the centrifugal separator 3.

Next, the controller 100 performs step S16. At step S16, the operation controller 118 controls the robot 10 to operate the centrifugal separator 3 so as to subject the composite container 60 to centrifugal separation processing. The centrifugal separation processing causes the liquid in the second container 80 of the composite container 60 to move into the first container 70 while dissolving the specimen on the filter 85. Thus, the specimen absorbed on the filter 85 is collected in the first container 70.

Next, the controller 100 performs step S17. At step S17, the transfer controller 111 controls the robot 10 to hold the composite container 60 in the centrifugal separator 3, similarly to step S01, and to return the composite container 60 to the platform 40.

Next, the controller 100 performs step S18. At step S18, the transfer controller 111 controls the robot 10 to perform positioning of the strap 74 of the composite container 60 returned to the platform 40. For example, the transfer controller 111 controls the robot 10 to perform the positioning of the strap 74 by following a procedure similar to the procedure of step S02.

Next, the controller 100 performs step S19. At step S19, the lid opening controller 112 controls the robot 10 to open the lid 90 of the composite container 60. For example, the lid opening controller 112 controls the robot 10 to open the lid 90 by following a procedure similar to the procedure of step S05.

Next, the controller 100 performs step S21. At step S21, the taking controller 114 controls the robot 10 to take the second container 80 out of the first container 70 of the composite container 60. After step S19, the controller 100 may perform step S20 before step S21. At step S20, the swing controller 113 controls the robot 10 to alternate effecting the first force to incline the second container 80 in the first direction relative to the first container 70 with effecting the second force to incline the second container 80 in the second direction relative to the first container 70.

For example, the swing controller 113 controls the robot 10 to follow a procedure similar to the procedure of step S06 so as to alternate effecting the first force to the second container 80 with effecting the second force to the second container 80. The taking controller 114 controls the robot 10 to take out the second container 80 by following a procedure similar to the procedure of step S07.

Next, the controller 100 performs step S22. At step S22, the transfer controller 111 controls the robot 10 to transfer the second container 80 that has been taken out at step S21 and to discharge the second container 80.

Next, the controller 100 performs step S23. At step S23, the lid closing controller 117 controls the robot 10 to cover the first opening 72 of the first container 70 housing the specimen using the lid 90, which is connected to the first container 70. For example, the lid closing controller 117 controls the robot 10 to cover the first opening 72 using the lid 90 by following a procedure similar to the procedure of step S09.

Next, the controller 100 performs step S24. At step S24, the transfer controller 111 controls the robot 10 to hold the first container 70, similarly to step S03, and to transfer the first container 70 into a container such as a freezer and an incubator. Thus, following the procedure for collecting a specimen ends.

3. Advantageous Effects of this Embodiment

The method for processing a specimen performed by the specimen processing system 1 includes controlling the robot 10 to open the lid 90 of the composite container 60; after the lid 90 has been opened; controlling the robot 10 to take the second container 80 out of the first container 70; and after the second container 80 has been taken out of the first container 70, controlling the robot 10 to cover the first opening 72 using the lid 90.

Although the use of the composite container 60 makes various kinds of specimen processing viable, the use of the composite container 60 necessitates various kinds of work compared with the use of an single-body container. The method for processing a specimen pertained by the specimen processing system 1 according to this embodiment enables the various kinds of work to be handled by the robot 10 alone. Thus, varying kinds of specimen processing can be handled by as simple a configuration as the robot 10.

The method for processing a specimen performed by the specimen processing system 1 according to this embodiment may further include, before controlling the robot 10 to take the second container 80 out of the first container 70, controlling the robot 10 to alternate effecting the first force to incline the second container 80 in the first direction relative to the first container 70 with effecting the second force to incline the second container 80 in the second direction relative to the first container 70. This step releases the engagement between the first container 70 and the second container 80 before the second container 80 is taken out of the first container 70, improving reliability in taking out the second container 80.

The robot 10 includes the two fingers 20A and 20B to hold the second container 80. The above-described first direction may be a direction toward one finger, and the above-described second direction may be a direction toward the other finger. The configuration using the two fingers 20A and 20B to hold the second container 80 facilitates the attempt to simplify the device configuration. With this configuration, the second container 80 may become distorted when the second container 80 is held by the two fingers 20A and 20B. Specifically, the second container 80 may become distorted in the direction in which the fingers 20A and 20B are opposed to each other (Y axis direction in FIG. 3). In Y axis direction, there is more room for making inclination effective for the second container 80 relative to the first container 70. In the direction orthogonal to the direction in which the fingers 20A and 20B are opposed to each other (Z axis direction in FIG. 3), the second container 80 may expand. In Z axis direction, there is less room for making inclination effective for the second container 80 relative to the first container 70. In view of this situation, the method for processing a specimen pertained by the specimen processing system 1 according to this embodiment includes alternating effecting a force to incline the second container 80 toward the one finger with effecting a force to incline the second container 80 toward the other finger. This improves reliability in moving the second container 80 and thus improves reliability in releasing the engagement between the first container 70 and the second container 80.

Controlling the robot 10 to alternate effecting a force to incline the second container 80 in the first direction with effecting a force to incline the second container 80 in the second direction may include controlling the robot 10 to move the protrusion portion 82 away from the first container 70 while alternating effecting the force to incline the second container 80 in the first direction with effecting the force to incline the second container 80 in the second direction. Specifically, the protrusion portion 82 is moved away from the first container 70 at the timing when the engagement between the first container 70 and the second container 80 is released. This configuration further facilitates the operation to take the second container 80 out of the first container 70.

The composite container 60 may further include the strap 74, which connects the lid 90 with the circumference of the first opening 72 of the first container 70. Controlling the robot 10 to cover the first opening 72 using the lid 90 may include controlling the robot 10 to move the lid 90 to a position corresponding to the first opening 72; controlling the robot 10 to cause a portion of the robot 10 contacting the outer surface of the lid 90 to move toward the first opening 72; and after the portion of the robot 10 contacting the outer surface of the lid 90 has moved to the first opening 72, controlling the robot 10 to cause the portion of the robot 10 contacting the outer surface of the lid 90 to move along the plane P1 of the first opening 72.

Advantageous effects of this configuration will be more readily appreciated by a comparison of this configuration with a comparative procedure for covering an opening a single-body container (for example, a micro-tube), without a second container, using a lid. As illustrated in FIG. 18A, a container 700 includes a body 701, a lid 710, and a strap 704. The body 701 has a tubular shape, similarly to the body 71, and is closed at one end and open at another end. The other end the body 701 is an opening 702, which is similar to the first opening 72. The container 700 includes a flange 703, which may be similar to the first flange 73. The flange 703 surrounds the opening 702 and extends outward beyond the body 701. In the following description of the container 700, terms such as "downward", "down", "below", and "under" may occasionally be used to refer to the direction toward the closed end of the body 701, and terms such as "upward", "up", and "above" may occasionally be used to refer to the direction toward the open end of the body 701.

The lid 710 is capable of covering the opening 702, and includes a fittable portion 711 and a flange 712. The finable portion 711 and the flange 712 may respectively be similar to the fittable portion 91 and the flange 92. The fittable portion 711 has a cylindrical structure fittable with the inner surface of the opening 702. The flange 712 has a plate structure that is disposed on top of the fittable portion 711 and that extends outward beyond the outer circumference of the fittable portion 711. The lid 710 may include an extending portion 713. The extending portion 713 extends outward from the outer circumference of the flange 712.

The strap 704 is an elastically deformable strip, similarly to the strap 74. The strap 704 has one end connected to the outer circumference of the flange 703 and another end connected to the outer circumference of the flange 712. The connection portion at which the strap 704 and the flange 712 are connected to each other is located at a position opposite to the extending portion 713 on the outer circumference of the flange 712. The strap 704 has a length smaller than the length of the strap 74.

Description will be made with regard to a procedure for controlling the robot 10 to cover the opening 702 of the container 700 using the lid 710. As illustrated in FIGS. 18A, 18B, 18C, 18D, 18E, and 18F, this control procedure includes controlling the robot 10 to move the lid 710 to a position corresponding to the opening 702; controlling the robot 10 to cause a portion of the robot 10 contacting the outer surface of 714 of the lid 710 to move toward the opening 702; and after the portion of the robot 10 contacting the outer surface of 714 of the lid 710 has moved to the opening 702, controlling the robot 10 to cause the portion of the robot 10 contacting the outer surface of 714 of the lid 710 to move away from the outer surface of 714 of the lid 710, instead causing the portion of the robot 10 contacting the outer surface of 714 of the lid 710 to move along plane P4 of the opening 702. The plane P4 of the opening 702 refers to the open surface of the opening 702 (for example, the top surface of the body 701).

As illustrated in FIG. 18A, the lid closing controller 117 controls the robot 10 to position the fingers 20A and 20B on both sides of the standing lid 710. Then, as illustrated in FIG. 18B, the lid closing controller 117 controls the robot 10 to contact the lid 710 using the distal end of the finger 20B, which is on the side of the outer surface of 714 of the lid 710, and to move the lid 710 to a position at which to cover the opening 702.

Then, as illustrated in FIG. 18C, the lid closing controller 117 controls the robot 10 to make the distal end of the finger 20B contact the extending portion 713 of the outer surface 714 and to move the distal end of the finger 20B toward the opening 702. The lid closing controller 117 controls the robot 10 to cause the distal end of the finger 20B to move toward the opening 702 so as to press at least one portion of the fittable portion 711 to a deepest possible position in the opening 702. For example, the lid closing controller 117 controls the robot 10 to cause the distal end of the finger 20B to move toward the first opening 702 to a distance at which a portion of the lid 710 unfitted in the opening 702 is interfered and another portion of the lid 710 completely fitted in the opening 702 is not interfered. More specifically, the lid closing controller 117 controls the robot 10 to make the distal end of the finger 20B move to a distance equivalent to the thickness of the flange 712 so as to approach the top surface of the body 701. By moving the distal end of the finger 20B toward the opening 702, the extending portion 713 side of the lid 710 is pressed toward the opening 702 and the extending portion 713 side of the fittable portion 711 is pressed into the opening 702.

Then, as illustrated in FIG. 18D, the lid closing controller 117 controls the robot 10 to cause the distal end of the finger 20B to move away from the outer surface of 714 of the lid 710, instead of causing the distal end of the finger 20B to move along the plane P4 of the opening 702.

Then, as illustrated in FIG. 18E, the lid closing controller 117 controls the robot 10 to cause the distal end of the finger 20B to move toward the strap 704.

Then, as illustrated in FIG. 18F, the lid closing controller 117 controls the robot 10 to cause the distal end of the finger 20B to move toward the opening 702 at a position corresponding to the strap 704 side of the lid 710. The distance over which the distal end of the finger 20B moves is similar to the distance over which the distal end of the finger 20B would move toward the opening 702 on the side of the extending portion 713 of the lid 710. By causing the distal end of the finger 20B to move toward the opening 702, the strap 704 side of the lid 710 is pressed toward the opening 702. This ensures reliability in pressing the entire fittable portion 711 into the opening 702, making the lid 710 tightly fitted in the opening 702 and making the opening 702 reliably covered.

As described above, the length of the strap 704 is smaller than the length of the strap 74. That is, the length of the strap 704 provides less of an allowance than the length of the strap 74 when the first opening 72 is covered using the lid 90. Since the length of the strap 704 provides less of an allowance, the strap 704 side of the lid 710 is more likely forced toward the body 701 by binding force. This ensures that when the portion of the robot 10 contacting the outer surface of 714 of the lid 710 is caused to move toward the opening 702, the force to press the lid 710 into the opening 702 more likely acts over the entire lid 710. Because of this configuration, if the binding force of the strap 704 is sufficiently binding, the opening 702 can be covered without causing the portion of the robot 10 contacting the outer surface of 714 of the lid 710 to move along the plane P4.

In contrast, the length of the strap 74 is larger than the length of the strap 704 by an amount that enables the lid 90 to cover the second opening 83, which is apart from the first opening 72. Therefore, when the lid 90 is covering the first opening 72, there is more of an allowance on the length of the strap 74. If the first opening 72 were covered using the lid 90 by following the procedure for covering the opening 702 using the lid 710, a portion of the lid 90 on the extending portion 93 side may rise when the finger 20B moves away from the outer surface 94 or when the finger 20B on the strap 74 side moves toward the first opening 72. Thus, the first opening 72 may not possibly be covered reliably.

In view of this situation, the procedure according to this embodiment includes controlling the robot 10 to, with the portion of the robot 10 contacting the outer surface of the lid 90 having moved to the first opening 72, cause the portion of the robot 10 contacting the outer surface of the lid 90 to move along the plane P1 of the first opening 72. Following this procedure eliminates or minimizes rising of a portion of the lid 90 already fitted in the first opening 72 while at the same time pressing into the first opening 72 a portion of the lid 90 yet to be fitted in the first opening 72. As a result, the lid 90 is tightly fitted in the first opening 72.

Controlling the robot 10 to cause a portion of the robot 10 to move along the plane P1 of the first opening 72 may include controlling the robot 10 to cause the portion of the robot 10 to reciprocate between the side of the strap 74 and the side opposite to the strap 74. In this case, the portion of the robot 10 contacting the outer surface of 94 of the lid 90 is caused to move between the side of the strap 74, where rising is more likely, and the side opposite to the strap 74. This improves reliability in fitting the lid 90 in the first opening 72.

The method for processing a specimen performed by the specimen processing system 1 according to this embodiment may further include controlling the robot 10 to insert the second container 80 taken out of the first container 70 into the another first container 70; and controlling the robot 10 to cover the second opening 83 using the lid 90 connected to the another first container 70. Thus, varying kinds of specimen processing can be handled by as simple a configuration as this configuration.

In this embodiment, controlling the robot 10 to cover the second opening 83 using the lid 90 connected to the another first container 70 follows a procedure similar to the procedure for covering the first opening 72 using the lid 90. This, however, should not be construed in a limiting sense. Another possible embodiment is that controlling the robot 10 to cover the second opening 83 using the lid 90 connected to the another first container 70 follows a procedure similar to the procedure for covering the opening 702 of the single-body container 700 using the lid 710. Specifically, controlling the robot 10 to cover the second opening 83 using the lid 90 connected to the another first container 70 may include controlling the robot 10 to move the lid 90 to a position corresponding to the second opening 83; controlling the robot 10 to cause a portion of the robot 10 contacting the outer surface of 94 of the lid 90 to move toward the second opening 83; and after the portion of the robot 10 contacting the outer surface of 94 of the lid 90 has moved to the second opening 83, controlling the robot 10 to cause the portion of the robot 10 contacting the outer surface of 94 of the lid 90 to move away from the outer surface of 94 of the lid 90, instead of causing the portion of the robot 10 contacting the outer surface of 94 of the lid 90 to move along the plane P2 of the second opening 83. In the following description, causing the portion of the robot 10 contacting the outer surface 94 to move toward the second opening 83 will be referred to as "pushing step", and causing the portion of the robot 10 contacting the outer surface 94 to move along the plane P2 will be referred to as "sliding step".

Covering the second opening 83 using the lid 90 involves positioning the lid 90 farther away from the first container 70 than when covering the first opening 72 using the lid 90. Therefore, the length of the strap 74 provides less of an allowance when the second opening 83 is covered using the lid 90. Since the length of the strap 74 provides less of an allowance, the strap 74 side of the lid 90 is more likely forced toward the first container 70 by binding force. If the binding force of the strap 74 is sufficiently binding, the lid 90 may be tightly fitted in the second opening 83 by the pushing step alone. In this case, by omitting the sliding step, the time necessary for closing the lid 90 is shortened, resulting in improved work efficiency.

The composite container 60 may further include the first flange 73 and the second flange 84. The first flange 73 surrounds the first opening 72 and extends outward beyond the first container 70. The second flange 84 surrounds the second opening 83 and extends outward beyond the second container 80. The method for processing a specimen performed by the specimen processing system 1 according to this embodiment may further include controlling the robot 10 to, before controlling the robot 10 to open the lid 90, hold the composite container 60 between the first flange 73 and the second flange 84 and to transfer the composite container 60. This ensures that even though the protrusion portion 82 of the second container 80 protrudes beyond the first container 70, a portion adjacent to the edge of the entire container is held. This facilitates taking and returning of the composite container 60.

The specimen processing system 1 may include the rack 30 and the platform 40. The rack 30 stores composite containers 60. The platform 40 holds a processing object, namely, a composite container 60 taken out of the rack 30. The rack 30 may include the depressions 33. The depressions 33 each receive the strap 74 of the composite container 60. Positioning the strap 74 on the platform 40 simplifies the operations to open and close the lid 90. However, if a configuration to position the strap 74 is provided on the platform 40, the configuration may interfere with the operations with respect to the lid 90. In view of this situation, the rack 30 is separate from the platform 40, and the position of the strap 74 on the rack 30 is determined in advance. This prevents the position of the strap 74 from varying on the platform 40. As a result, the operations to open and close the lid 90 are simplified.

Obviously, numerous modifications and variations of the present disclosure are possible in light of the above teachings. It is therefore to be understood that within the scope of the appended claims, the present disclosure may be practiced otherwise than as specifically described herein.

What is claimed as new and desired to be secured by Letters Patent of the United States is:

1. A method for processing a specimen, comprising:
controlling a robot to open a lid of a composite container comprising a first container and a second container, wherein the composite container includes the first container having a first opening, and the second container having an insertion portion insertable into the first container through the first opening, a protrusion portion protrudable through the first opening, and a second opening formed on the protrusion portion and coverable by the lid;
after the lid has been opened, controlling the robot to take the second container out of the first container; and
after the second container has been taken out of the first container, controlling the robot to cover the first opening using the lid,
wherein the robot is controlled using a controller comprising circuitry configured to control the robot to open the lid of the composite container, take the second container out of the first container, and to cover the first opening using the lid.

2. The method according to claim 1, further comprising, before the controlling of the robot to take the second container out of the first container, controlling the robot to alternate effecting a first force to incline the second container in a first direction relative to the first container with effecting a second force to incline the second container in a second direction relative to the first container.

3. The method according to claim 2, wherein the robot comprises a first finger and a second finger that are configured to hold the second container.

4. The method according to claim 2, wherein the controlling of the robot to alternate effecting the first force with effecting the second force comprises controlling the robot to move the protrusion portion away from the first container while alternating effecting the first force with effecting the second force.

5. The method according to claim 1, wherein the composite container further comprises a strap connecting a circumference of the first opening with the lid, and the controlling of the robot to cover the first opening using the lid comprises controlling the robot to move the lid to a position corresponding to the first opening, controlling the robot to cause a portion of the robot contacting an outer surface of the lid to move toward the first opening, and after the portion of the robot contacting the outer surface of the lid has moved to the first opening, controlling the robot to cause the portion of the robot to move along a plane of the first opening.

6. The method according to claim 5, wherein the controlling of the robot to cause the portion of the robot to move along the plane of the first opening comprises controlling the robot to cause the portion of the robot to reciprocate between a first side of the plane by the strap and a second side of the plane opposite to the first side.

7. The method according to claim 5, further comprising:
controlling the robot to insert the second container taken out of the first container into another first container; and
controlling the robot to cover the second opening using another lid connected with the another first container.

8. The method according to claim 7, wherein the controlling of the robot to cover the second opening using the another lid connected to the another first container comprises controlling the robot to move the another lid to a position corresponding to the second opening, controlling the robot to cause a portion of the robot contacting an outer surface of the another lid to move toward the second opening, and after the portion of the robot contacting the outer surface of the another lid has moved to the second opening, controlling the robot to cause the portion of the robot to move away from the outer surface of the another lid without moving along a plane of the second opening.

9. The method according to claim 1, further comprising:
before the controlling of the robot to open the lid of the composite container, controlling the robot to hold a portion of the composite container between a first flange and a second flange of the composite container so as to transfer the composite container,
wherein the first flange is disposed at a circumference of the first opening and extending outward from the first container, and the second flange is disposed at a circumference of the second opening and extending outward from the second container.

10. A specimen processing system, comprising:
a robot; and
a controller comprising circuitry configured to control the robot to open a lid of a composite container,
wherein the composite container includes a first container having a first opening, and a second container having an insertion portion insertable into the first container through the first opening, a protrusion portion protrudable through the first opening, and a second opening formed on the protrusion portion and coverable by the lid, and the circuitry of the controller is further configured to control the robot to, after the robot has opened the lid, take the second container out of the first container, and control the robot to, after the robot has taken the second container out of the first container, cover the first opening using the lid.

11. The specimen processing system according to claim 10, further comprising:
a rack configured to store the composite container; and
a platform configured to support the composite container after the composite container has been taken out of the rack as a processing object,
wherein the composite container further comprises a strap connecting a circumference of the first opening with the lid, and the rack comprises a depression formed to receive the strap of the composite container when the composite container is stored in the rack.

12. The method according to claim 3, wherein the controlling of the robot to alternate effecting the first force with effecting the second force comprises controlling the robot to, while alternating effecting the first force with effecting the second force, move the protrusion portion away from the first container.

13. The method according to claim 2, wherein the composite container further comprises a strap connecting a circumference of the first opening with the lid, and the controlling of the robot to cover the first opening using the lid comprises controlling the robot to move the lid to a position corresponding to the first opening, controlling the robot to cause a portion of the robot contacting an outer surface of the lid to move toward the first opening, and after the portion of the robot contacting the outer surface of the lid has moved to the first opening, controlling the robot to cause the portion of the robot to move along a plane of the first opening.

14. The method according to claim 3, wherein the composite container further comprises a strap connecting a circumference of the first opening with the lid, and the controlling of the robot to cover the first opening using the lid comprises controlling the robot to move the lid to a position corresponding to the first opening, controlling the robot to cause a portion of the robot contacting an outer surface of the lid to move toward the first opening, and after the portion of the robot contacting the outer surface of the lid has moved to the first opening, controlling the robot to cause the portion of the robot to move along a plane of the first opening.

15. The method according to claim 4, wherein the composite container further comprises a strap connecting a circumference of the first opening with the lid, and the controlling of the robot to cover the first opening using the lid comprises controlling the robot to move the lid to a position corresponding to the first opening, controlling the robot to cause a portion of the robot contacting an outer surface of the lid to move toward the first opening, and after the portion of the robot contacting the outer surface of the lid has moved to the first opening, controlling the robot to cause the portion of the robot to move along a plane of the first opening.

16. The method according to claim 12, wherein the composite container further comprises a strap connecting a circumference of the first opening with the lid, and the controlling of the robot to cover the first opening using the lid comprises controlling the robot to move the lid to a position corresponding to the first opening, controlling the robot to cause a portion of the robot contacting an outer surface of the lid to move toward the first opening, and after the portion of the robot contacting the outer surface of the lid has moved to the first opening, controlling the robot to cause the portion of the robot to move along a plane of the first opening.

17. The method according to claim 13, wherein the controlling of the robot to cause the portion of the robot to move along the plane of the first opening comprises controlling the robot to cause the portion of the robot to reciprocate between a first side of the plane by the strap and a second side of the plane opposite to the first side.

18. The method according to claim 14, wherein the controlling of the robot to cause the portion of the robot to move along the plane of the first opening comprises controlling the robot to cause the portion of the robot to reciprocate between a first side of the plane by the strap and a second side of the plane opposite to the first side.

19. The method according to claim 15, wherein the controlling of the robot to cause the portion of the robot to move along the plane of the first opening comprises controlling the robot to cause the portion of the robot to reciprocate between a first side of the plane by the strap and a second side of the plane opposite to the first side.

20. The method according to claim 16, wherein the controlling of the robot to cause the portion of the robot to move along the plane of the first opening comprises controlling the robot to cause the portion of the robot to reciprocate between a first side of the plane by the strap and a second side of the plane opposite to the first side.

* * * * *